(12) United States Patent
Rasnow et al.

(10) Patent No.: US 7,700,928 B2
(45) Date of Patent: Apr. 20, 2010

(54) APPARATUS AND METHOD FOR INTERLEAVING DETECTION OF FLUORESCENCE AND LUMINESCENCE

(75) Inventors: Brian Rasnow, Newbury Park, CA (US); Chuck Z. Li, Thousand Oaks, CA (US)

(73) Assignee: Etaluma, Inc., Carlsbad, CA (US)

( * ) Notice: Subject to any disclaimer, the term of this patent is extended or adjusted under 35 U.S.C. 154(b) by 26 days.

(21) Appl. No.: 11/627,259

(22) Filed: Jan. 25, 2007

(65) Prior Publication Data

US 2008/0179539 A1    Jul. 31, 2008

(51) Int. Cl.
G01N 21/64 (2006.01)
(52) U.S. Cl. .................................... 250/458.1
(58) Field of Classification Search ................ 250/458.1
See application file for complete search history.

(56) References Cited

U.S. PATENT DOCUMENTS

| | | | |
|---|---|---|---|
| 4,714,345 A | 12/1987 | Schrader | |
| 5,184,020 A | 2/1993 | Hearst et al. | |
| 5,329,353 A | 7/1994 | Ichimura et al. | |
| 5,355,215 A | 10/1994 | Schroeder et al. | |
| 5,377,003 A | 12/1994 | Lewis et al. | |
| 5,644,388 A | 7/1997 | Maekawa et al. | |
| 5,683,661 A | 11/1997 | Hearst et al. | |
| 5,686,960 A | 11/1997 | Sussman et al. | |
| 5,714,388 A | 2/1998 | Kusnetz et al. | |
| 5,774,214 A | 6/1998 | Prettyjons et al. | |
| 5,854,648 A | 12/1998 | Hanabusa | |
| 5,928,907 A * | 7/1999 | Woudenberg et al. ...... | 435/91.2 |
| 5,953,133 A | 9/1999 | Fujimiya et al. | |
| 6,039,925 A | 3/2000 | Nemoto | |
| 6,057,163 A | 5/2000 | McMillan et al. | |
| 6,091,502 A * | 7/2000 | Weigl et al. ................. | 356/416 |

(Continued)

FOREIGN PATENT DOCUMENTS

WO    WO 0006991    2/2000

OTHER PUBLICATIONS

Cobbold et al. (1983) *J. Cell Sci.* 61:123-136.

(Continued)

*Primary Examiner*—David P Porta
*Assistant Examiner*—Marcus H Taningco
(74) *Attorney, Agent, or Firm*—Michael Blaine Brooks, PC; Michael B. Brooks

(57) ABSTRACT

An apparatus is provided that is capable of interleaving detection of fluorescence and luminescence signals emitted from a plurality of samples. The apparatus is suitable for analysis of samples containing single cells or tissues up to and including living organisms. It contains an optical assembly or "sandwich" for producing a spectrally pure and spatially dispersed light source for illuminating the sample. The invention also provides a plurality of optical sandwiches that can be variously geometrically arranged and their intensities programmed to create spatially uniform illumination over a large sample. The invention further provides an apparatus having at least one of the optical sandwich and a detector system capable of interleaving detection of fluorescent and luminescent signals when a suitable sample is illuminated by the light source of the optical sandwich. Methods for preparing samples and using the sandwiches, arrays and apparatus, are further provided by this invention. A method for interleaving detection of fluorescent and luminescent signals emitted from a plurality of samples is disclosed.

27 Claims, 16 Drawing Sheets

U.S. PATENT DOCUMENTS

| | | | |
|---|---|---|---|
| 6,097,025 A | 8/2000 | Modlin et al. | |
| 6,313,960 B2 | 11/2001 | Marquiss et al. | |
| 6,466,316 B2 | 10/2002 | Modlin et al. | |
| 6,571,118 B1 * | 5/2003 | Utzinger et al. | 600/476 |
| 6,597,450 B1 | 7/2003 | Andrews et al. | |
| 6,678,577 B1 | 1/2004 | Stylli et al. | |
| 6,680,025 B2 | 1/2004 | Hearst et al. | |
| 6,746,864 B1 | 6/2004 | McNeil et al. | |
| 6,800,452 B1 | 10/2004 | McNeil et al. | |
| 6,825,921 B1 | 11/2004 | Modlin et al. | |
| 6,930,314 B2 | 8/2005 | Jackson et al. | |
| 6,970,240 B2 | 11/2005 | Oldham et al. | |
| 6,982,421 B2 | 1/2006 | Sato et al. | |
| 6,982,431 B2 | 1/2006 | Modlin et al. | |
| 6,985,225 B2 | 1/2006 | Bechem et al. | |
| 7,115,384 B2 | 10/2006 | Clark et al. | |
| 7,170,597 B1 * | 1/2007 | Hooper et al. | 356/317 |
| 7,199,377 B2 | 4/2007 | Wulf et al. | |
| 7,199,879 B2 | 4/2007 | Harju et al. | |
| 2002/0064867 A1 | 5/2002 | Clark et al. | |
| 2002/0088952 A1 * | 7/2002 | Rao et al. | 250/559.45 |
| 2002/0197740 A1 * | 12/2002 | Hansen et al. | 436/525 |
| 2003/0044967 A1 * | 3/2003 | Heffelfinger et al. | 435/287.2 |
| 2003/0076281 A1 | 4/2003 | Morgan et al. | |
| 2003/0170141 A1 | 9/2003 | Hearst et al. | |
| 2003/0230728 A1 | 12/2003 | Dai et al. | |
| 2004/0014202 A1 | 1/2004 | King et al. | |
| 2004/0033530 A1 | 2/2004 | Awrey et al. | |
| 2004/0061914 A1 * | 4/2004 | Miyawaki et al. | 359/1 |
| 2004/0202577 A1 | 10/2004 | McNeil et al. | |
| 2005/0062969 A1 | 3/2005 | Harju et al. | |
| 2005/0099622 A1 | 5/2005 | Caracci et al. | |
| 2005/0122521 A1 | 6/2005 | Katzlinger et al. | |
| 2005/0190366 A1 | 9/2005 | Boege et al. | |
| 2005/0218338 A1 | 10/2005 | Wulf et al. | |
| 2005/0250173 A1 | 11/2005 | Davis et al. | |
| 2005/0260741 A1 * | 11/2005 | Albertson et al. | 435/287.2 |
| 2005/0285129 A1 | 12/2005 | Jackson et al. | |
| 2006/0068490 A1 * | 3/2006 | Tang et al. | 435/287.2 |
| 2007/0258858 A1 | 11/2007 | Rasnow et al. | |
| 2008/0031781 A1 | 2/2008 | Rasnow et al. | |

OTHER PUBLICATIONS

Edwards et al. (2004) *Curr. Opin. Chem. Biol.* 8:392-398.
Schubert and Kim (2005) "Solid-state light sources getting smart" *Science* 308:1274-1278.
Shimomura et al. (1984) *Biochem J.* 228:745-749.

* cited by examiner

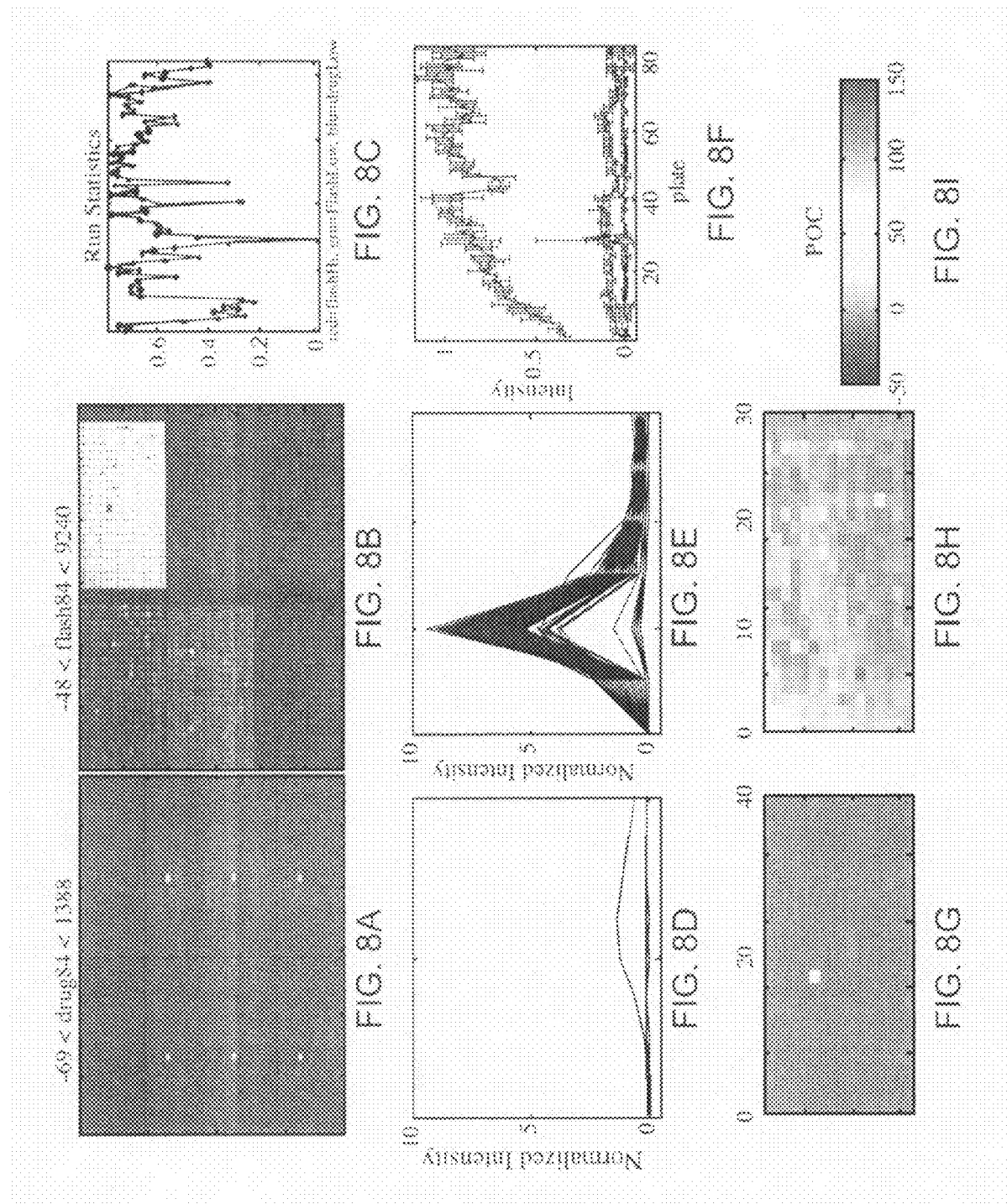

Integration Parameters

ROI and Normalization file

[fluor23.mat ▼]

| | |
|---|---|
| Temporal Algorithm | sum ▼ |
| Flash Frames | 6:40 |
| Drug Frames | 5:60 |
| Mask Algorithm | mean ▼ |
| Mask Frames | 10:25 |
| Spatial Algorithm | fixed percentage ▼ |
| Spatial Parameters | 0.15 0.95 |

POC Control Columns

| | | | |
|---|---|---|---|
| Flash high | 11 12 | low | 23 24 |
| Drug low1 | 11 12 | low2 | 23 24 |
| Color scale range | | -50 150 | |

[Update]  [Revert]

[Load Protocol]  [Save Protocol]

FIG. 13

APPARATUS AND METHOD FOR INTERLEAVING DETECTION OF FLUORESCENCE AND LUMINESCENCE

FIELD OF THE INVENTION

This disclosure relates to a variety of apparatus capable of interleaving detection of luminescent and fluorescent signals and methods for their use. The apparatus and methods are particularly suited for high throughput biochemical analysis of multiple samples, for example, within a microtiter plate.

BACKGROUND OF THE INVENTION

High throughput, multi-well assay systems are routinely used for target identification and lead optimization during drug development. More recently, high throughput systems have been proposed as a means to isolate high expressing cell lines necessary for commercial production of recombinant proteins. Edwards et al. (2004) Curr. Opin. Chem. Biol. 8:392-398 and U.S. Patent Publ. No. 2004/0033530A.

Fluorescence and bioluminescence labels typically are used in high throughput screening of biological samples. In techniques using fluorescence, cells of various tissue types are incubated in the presence of a fluorescent dye which is used as a label to identify a known target, marker or analyte. The signal emitted from the dye, after binding to the target, marker or analyte, is then detected using a camera or other detector. Disadvantages of fluorescent detection for biological assays include the small intensity of the fluorescence signal compared to the excitation intensity, the presence of background or nonspecific fluorescence, and interference from other fluorescence compounds than the label. For example, when measuring cells in a monolayer or microtiter plate, the cell layers are first illuminated with a light of a first wavelength and emission at a second wavelength is monitored as by a photodetector device. If any of the first wavelength leaks through the emission filter to the detector, or if any second wavelength is present in the excitation and reflects to the detector, they will contaminate the fluorescence signal emitted from the sample. Fluorescent label that is not completely washed or quenched and fluorescent compounds in the proximity of the cells can also affect the fluorescence signal from the label.

Bioluminescent labels avoid many of the drawbacks of fluorescence because they don't rely on excitation light and the sharp spectral filtering required to separate excitation and emission light. The major challenge of detecting bioluminescence is its inherently weaker intensity. Whereas with fluorescence, the signal can be increased by increasing the excitation intensity, dye concentration, and target density, bioluminescence is often limited by biological constraints on luminophore concentration.

Several multiplex systems are commercially available for use in high throughput screening but for various reasons, none of these interleave fluorescence and high-sensitivity luminescence imaging detection. For example, U.S. Pat. Nos. 6,057,163 and 6,985,225 describe sample reading devices for multiple sample analysis within a multi-well plate. Interference from adjacent samples is minimized by using a mask to isolate those wells or samples for detection while covering those which are not under analysis at that time. However, the process of masking and unmasking samples to be detected increases the amount of time necessary for calibration and analysis of a sample array. It also introduces moving mechanisms to automate the masking and unmasking of the samples in the device which increases the probability of device malfunction and error.

Moreover, none of these devices are suitable for multifunctional analysis of a complex biological or chemical sample using both fluorescent and luminescent labels integrated with fluidic transfers. Thus, a system that provides multi-functional fluidics and multimodal imaging of a complex sample which is amenable to automation and high throughput systems would be an advance over the prior art.

SUMMARY OF THE INVENTION

Fluorescence and luminescence are both commonly practiced methods for detecting biomolecular interactions but have not heretofore been combined in a manner that allows substantially concurrent, high throughput parallel detection of these modalities. To achieve this result, an apparatus is provided that is capable of interleaving detection of fluorescence and luminescence signals emitted from a plurality of samples.

The apparatus is suitable for analysis of samples containing single cells or tissues up to and including living organisms. It contains an optical assembly (termed an "optical sandwich" herein) for producing a spectrally pure and spatially dispersed light source for illuminating the sample. The components of the assembly include a light source, a high numerical aperture collimation lens, an excitation filter and a diffuser that in combination produce a spectrally pure and spatially dispersed illumination. Two or more sandwiches or assemblies can be combined into an optical array to additionally produce a spatially uniform illumination. Additional modifications of the optical sandwich are described infra.

In one aspect, the optical sandwich is an element of an apparatus for interleaving detection of fluorescent and luminescent signals. In this aspect of the invention, an apparatus is provided which contains a sample receiving device for receiving a sample container, the optical sandwich as described herein and a detector system capable of interleaving detection of fluorescent and luminescent signals emitted from at least one of the samples contained within the sample container, the samples containing fluorescent or luminescent labels. Additional modifications of the device are described infra. The detector system comprises a detector lens, an emission filter and a sensor, for example an imaging sensor.

The optical sandwich, the array and the apparatus, or device, are useful in methods for illumination and detection of fluorescent signals emitted from samples that have been suitably prepared with fluorescent label. These same samples may also contain luminescent molecules. In one aspect, the sample has been prepared for fluorescent and/or luminescent analysis and interleaving detection thereof. Fluorescent and/or luminescent signals emitted from a plurality of samples can be detected in a high-throughput manner.

The present invention also relates to a method for interleaving detection of fluorescent and luminescent signals emitted from a plurality of samples, which involves detecting fluorescent and luminescent signals produced by the plurality of samples. The fluorescence excitation light source is automatically turned off or shuttered during interleaved luminescence imaging. The method can be practiced using the apparatus of the present invention, or by using an alternative apparatus suitably modified as described herein.

BRIEF DESCRIPTION OF THE DRAWINGS

Exemplary embodiments will hereafter be described with reference to the accompanying drawings.

FIG. 3A is a detail of the rotating shaft. FIG. 3B shows how a plurality of rotating shafts, each containing a plurality of arrays, can be contained within a device of this invention.

FIGS. 8A through 8I show example output of a luminescence assay.

FIG. 13 depicts a user interface of integration parameters which control image data processing and visualization parameters of the screening system in accordance with an exemplary embodiment.

DETAILED DESCRIPTION OF THE INVENTION

Figure 1:
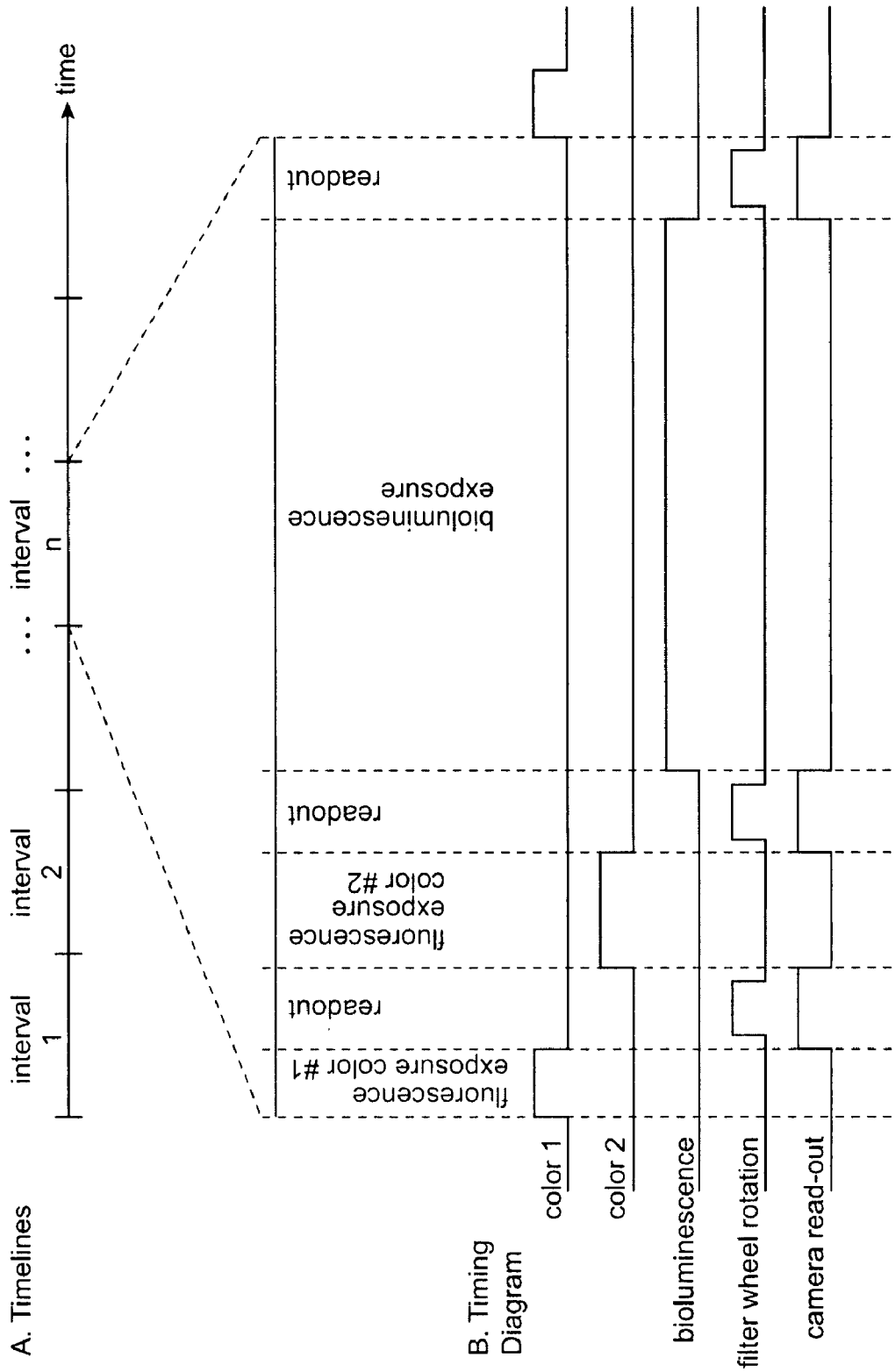
FIG. 1 is a timing diagram of interleaving detection of fluorescent and luminescent signals.

As used herein, the following terms are understood to have these defined meanings.

As used in the specification and claims, the singular form "a", "an" and "the" include plural references unless the context clearly dictates otherwise. For example, the term "a sample" includes a plurality of samples, including mixtures thereof such as a culture of cells of the same or different cell type or alternatively, a complex tissue sample.

As used herein, the term "comprising" is intended to mean that the systems and methods include the recited elements, but not excluding others. "Consisting essentially of" when used to define assemblies and methods, shall mean excluding other elements of any essential significance to the combination. "Consisting of" shall mean excluding more than trace elements of other components and substantial method steps.

It is to be understood, although not always explicitly stated that all numerical designations are preceded by the term "about". It also is to be understood, although not always explicitly stated, that the reagents described herein are merely exemplary and that equivalents of such are known in the art.

As used herein, the term "luminescent" refers to any substance or agent that is capable of exhibiting "luminescence", which is the emission of light by sources other than a hot, incandescent body. For purposes of the present invention, "luminescent" or "luminescence" does not include "fluorescent" or "fluorescence" or "photoluminescent" or "photoluminescence". Luminescence is caused by electronic transitions within a luminescent substance (or luminophore) from more energetic to less energetic states. Among several types are bioluminescence, chemiluminescence, electrochemiluminescence, electroluminescence, and triboluminescence, which are produced by chemical reactions, electrochemical reactions, electric discharges, and the rubbing or crushing of crystals, respectively. Molecules may be intrinsically and/or extrinsically luminescent, meaning that they are luminescent on their own or luminescent due to covalent and/or noncovalent association with another molecule.

The term "fluorescent" refers to any substance or agent that is capable of exhibiting "fluorescence" (or "photoluminescence"), which is the emission of light triggered by the molecular absorption of a photon with longer wavelength. Fluorescence thus is dependent on an "excitation light source" that is distinct from the longer wavelength fluorescence "emission" emanating from the fluorophore. Detection of fluorescence emission requires that a detector that responds only to the emission light and not to the excitation light As is known to those of skill in the art, the detectable response is a change in a property of the luminescence or fluorescence light, such as a change in the intensity, polarization, energy transfer, lifetime, and/or excitation or emission wavelength distribution. The detectable response may be simply detected, or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluoresecence assays, the detectable response may be generated directly using a luminophore or fluorophore associated with an assay component actually involved in binding, or indirectly using a luminophore or fluorophore associated with another (e.g., reporter or indicator) component.

As used herein, the term "spectral purity" refers to the ability of a fluorescence excitation source to emit pure excitation wavelengths, without emitting light at the longer fluorophore emission wavelengths. Cross-color contamination should be less than $10^{-5}$ to $10^{-6}$ (OD5-6) to achieve sensitive fluorescence detection. This is generally achieved with a sharp cut-off "excitation filter" as is known to those of skill in the art.

The term "spatial uniformity" refers to the system's ability to detect a uniform distribution of sample without significant (i.e., <2 fold) variation in sensitivity and signal-to-noise from anywhere within the image. Many imaging detectors do not have uniform sensitivity across their field of view. For example, a common artifact of optical systems is attenuation or "vignetting" away from the optical axis. This can be partially compensated for by illuminating the image plane with a complementary intensity pattern, as is described herein.

The term "interleaving" refers to and intends the accomplishment of multiple independent tasks in time division sequence.

Embodiments of the Invention

This invention provides a device or assembly capable of interleaving detection of fluorescence and luminescence emitted from a sample that has been suitably prepared for this interleaving detection. Major challenges to achieving sensitive fluorescence detection is achieving spectral purity, high brightness, and spatial uniformity over the extended area of the sample. For example, lasers can offer high spectral purity but their beam sizes tend to be small, brightest at their center, and it is difficult to spread their focused light uniformly over large areas. The optical sandwich described in further detail below achieves a high degree of spectral purity and brightness. Within the scope of the invention, multiple optical sandwiches can be assembled into arrays of the present invention to achieve excellent spatial uniformity of the collective system, as further described herein below. Applicants' invention achieves these results by incorporating some or all of the following: 1) arrays of non-uniformly spaced individual excitation sources; 2) driving each excitation source with independent currents; 3) using feedback control to adjust the currents; and 4) using an "optical sandwich" to filter and disperse the light from each excitation source. Furthermore, the invention encompasses: 1) an apparatus that contains the optical sandwich, a sample receiving system, and a detector system; and embodiments that include 2) a screening system with control software that enables the applications of interleaving imaging detection of fluorescence and luminescence.

The Optical Assembly or Optical Sandwich

Figure 2A:
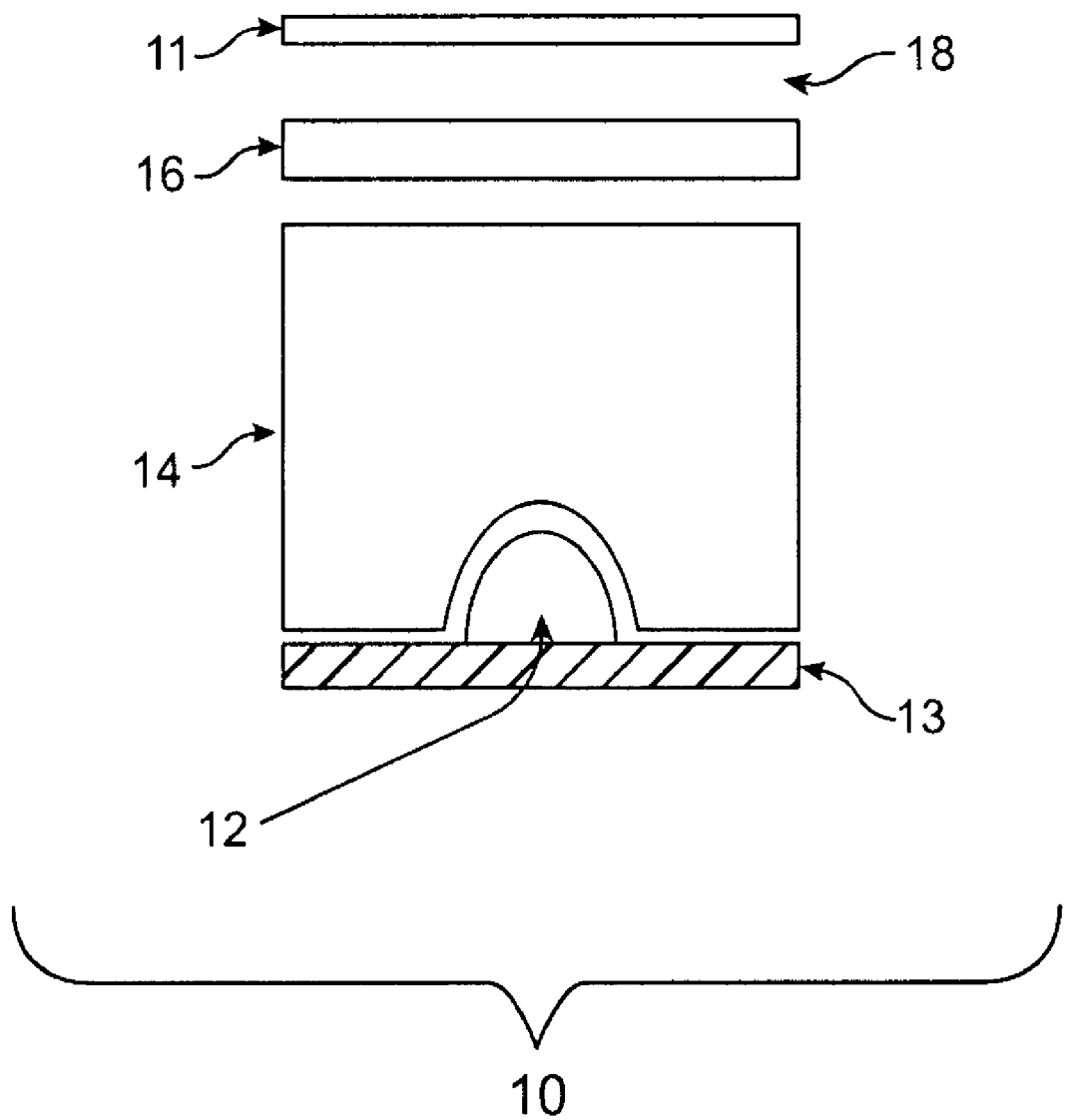
FIGS. 2A and 2B illustrate two embodiments of an optical sandwich.
Figure 2B:
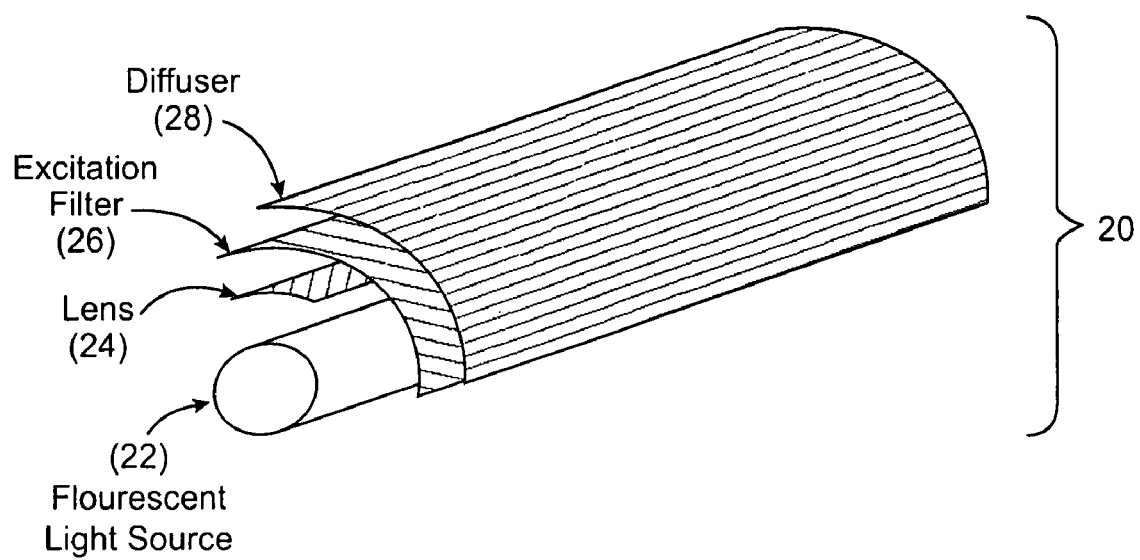

In one aspect, this invention provides an optical assembly or "optical sandwich" that includes but is not limited to a light source, a high numerical aperture collimation lens, an excitation filter (e.g., a sharp spectral band pass filter, a low pass filter or a high pass filter) and a diffuser. The components of the sandwich are arranged relative to each other to provide a spectrally pure and spatially dispersed illumination. FIGS. 2A and 2B are non-limiting examples of optical sandwiches.

Light Source: The light source element of the optical sandwich is capable of providing an illumination source to excite a fluorescent label in the sample when the light is properly filtered and dispersed. For the purpose of illustration only, examples of suitable light sources for use in the sandwich include but are not limited to a broad spectrum light source, a narrow spectrum light source, an ultra-bright light emitting diode (LED), a deuterium tube, a broad spectrum flashlamp, a fluorescent light source (e.g., a fluorescent tube or bulb), an ultraviolet LED, laser diodes, and a quartz-tungsten-halogen (QTH) bulb.

In one aspect, the assembly utilizes ultra-bright LEDs as the light source. Examples of such are known in the art and are commercially available from CREE or Lumiled as well as described in technical publications such as Schubert and Kim (2005) "Solid-state light sources getting smart." Science 308: 1274:1278. Details of their incorporation into a spectrally pure and spatially homogeneous fluorescence excitation source are described herein.

In another aspect, the light source of the optical sandwich is selected to produce any one or more of monochromatic or multichromatic, polarized or unpolarized, and coherent or incoherent light. Continuous sources produce substantially continuous illumination, whereas time-modulated sources produce time-modulated illumination.

The ultimate selection of the light source for use in the optical sandwich is based on the sample or samples to be illuminated and the fluorescent label or labels, when more than one is utilized or to be detected. One of skill in the art can determine the most effective light source based on the individual parameters of the sample, the label and the purpose of the assay.

Collimation Lens and Excitation Filter: A high numerical aperture collimation lens over the light source efficiently captures the emission and focuses it into a more collimated beam. This is counterproductive to dispersing the light over the spatial extent of the sample. However, collimating provides a more normal incidence of the light to the excitation filter surface directly above the lens. This improves the performance and efficiency of the filter, and thus provides better spectral purity of the filtered light (e.g., www.semrock.com/Catalog/Raman_SpectrumvsAOI.htm). The spectral leakage of the excitation filter dramatically increases with increasing incident angle. By focusing more photons through a filter at near normal incidence, the spectral leakage is significantly reduced. This leakage contributes to non-specific fluorescence background noise and reduces the sensitivity of the detector.

Examples of suitable excitation filters for use in the optical assembly of this invention include, but are not limited to, a sharp spectral band pass filter, a low pass filter and a high pass filter, which are commercially available from sources including Semrock, Omega, Chroma, and others.

Diffuser: The optical sandwich also includes a diffuser (exemplified in FIG. 2A (11) and FIG. 2B (28)) which serves to homogenize the light and disperse it more broadly across the sample. In particular, it eliminates any "hotspots" from the filament or junctions of the light source such as an LED. When the incident light has a divergence half angle of approximately 5 degrees, the diffuser expands the divergence angle to 15-60 degrees. Examples of diffusers for use in the sandwich of this invention include, but are not limited to a holographic diffuser (available commercially from e.g., Physical Optics Corp, Torrance, Calif.), frosted glass, opal glass and/or gradient diffuser. When a plurality of sandwiches are combined into an array (see infra) different diffusers can be used on different sandwiches to help achieve a spatially uniform excitation of the sample. For example, narrower dispersion at the corners can focus more light on the typically fainter sample corners, while the center sandwiches have broader dispersion to give broader illumination.

FIG. 2A illustrates one embodiment of the optical sandwich (10). In this embodiment, a high intensity LED (12) is the light source for fluorescence excitation, supported on a heat sink (13). Locate proximal to the LED (12) is a high numerical aperture lens (14). An excitation filter (16) and diffuser (11) creates the spectrally pure and spatially diffuse illumination. Located between the diffuser (11) and the filter (16) is a gap (18). The gap, for modulation of the amount of diffusion, is about 0 to about 1 cm thick. The gap contains any suitable optically transparent medium, such as, but not limited to, air, another gas, a liquid, glass, or a vacuum.

FIG. 2B illustrates a separate embodiment when the light source is a broadband fluorescent tube (22). The remaining elements of the sandwich are located in concentric rings around the fluorescent tube, moving from the tube to the diffuser and concentric to each other are the elements of a numerical aperture lens (24), an excitation filter (26) and a diffuser (28). In this embodiment, variable excitation filters (e.g., 26) serve to select the appropriate wavelength.

An Array of Optical Sandwiches

In a further aspect, a plurality of the optical sandwiches are combined and arranged into an array (see FIG. 3A, elements ((52), (54) and (56), for example) that illuminates the sample from various positions above, below, or around the sample and sample receiving device as long as the excitation light can illuminate the sample. When more than one light source is within the array ((52), (54) or (56)), the light sources are of the same color thereby emitting light of the same wavelength but can optionally vary in their intensity, current, or diffusion angle. The geometry of the light sources or sandwiches in the array can vary between or among the sandwiches and yet further, the spacing between the arrays can be uniform or non-uniform (see FIG. 6A). The number of sandwiches in the array is variable and includes without limitation, e.g., 2 or 3 or 4 or 5 or 6 or any integral amount that can exceed 10 or more.

Figure 3A:
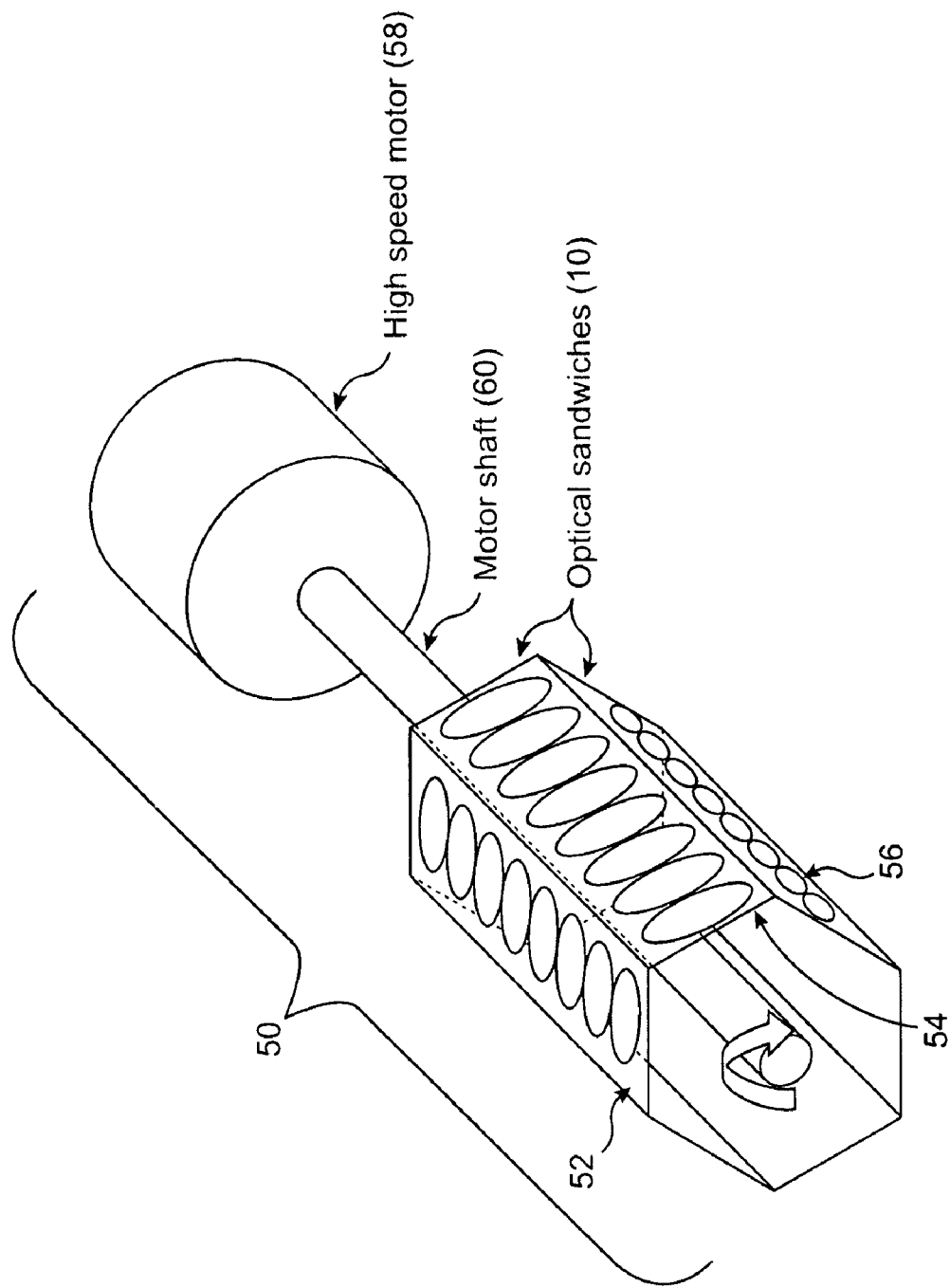
FIGS. 3A and 3B schematically show a plurality of arrays of optical sandwiches positioned on a rotating shaft.
Figure 3B:
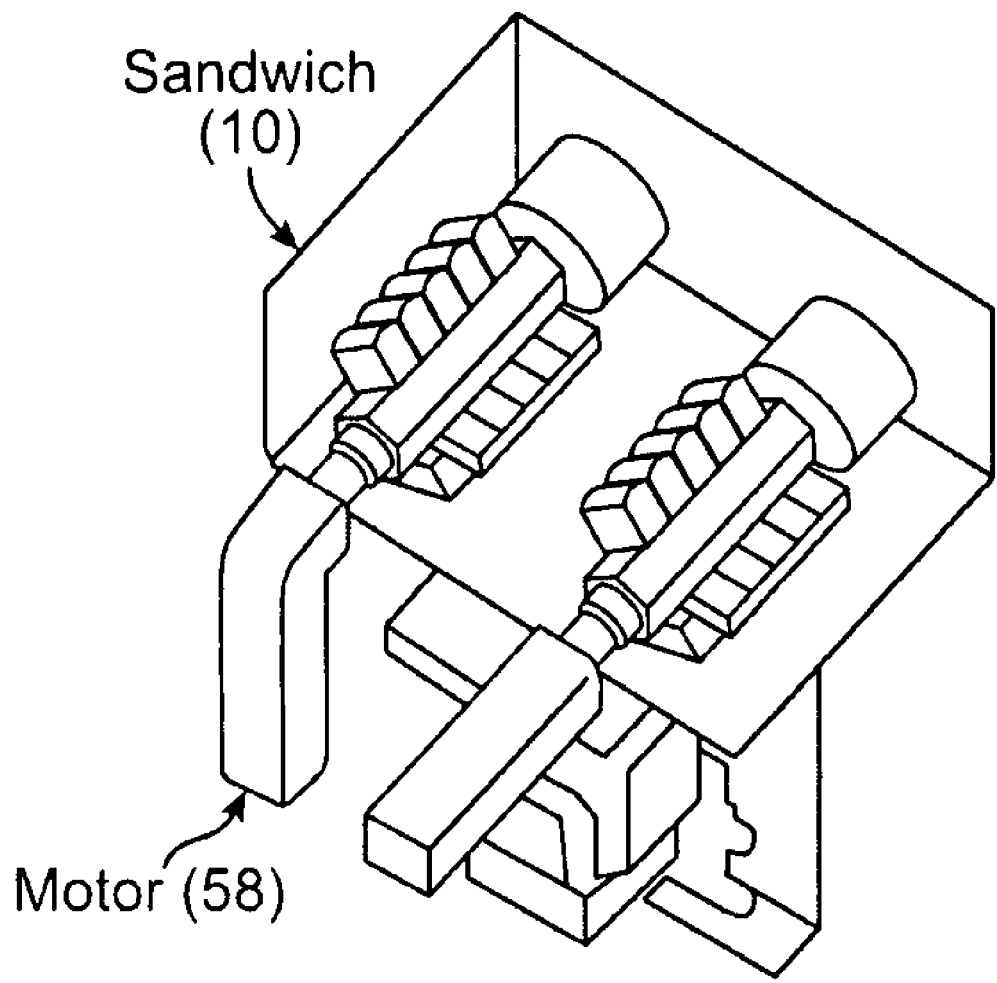

Multiple arrays of sandwiches emitting the same color can be further combined and arranged in various geometries which include, but are not limited to a plane, coupled to a linear actuator or a rotating shaft (see FIGS. 3A and 3B). While each sandwich within an array is of the same color (i.e., wavelength), the multiple or plurality of arrays are not so limited.

When the arrays are arranged on a plane, the axis of each sandwich within the array are approximately or substantially perpendicular to the plane and oriented in the approximate direction of the sample. In a further embodiment, the arrays are arranged substantially parallel to each other. When the arrays are contained on a rotating shaft, the axis of each sandwich is substantially parallel or nearly parallel to each other and perpendicular or substantially perpendicular to the axis of the shaft.

Figure 6A:
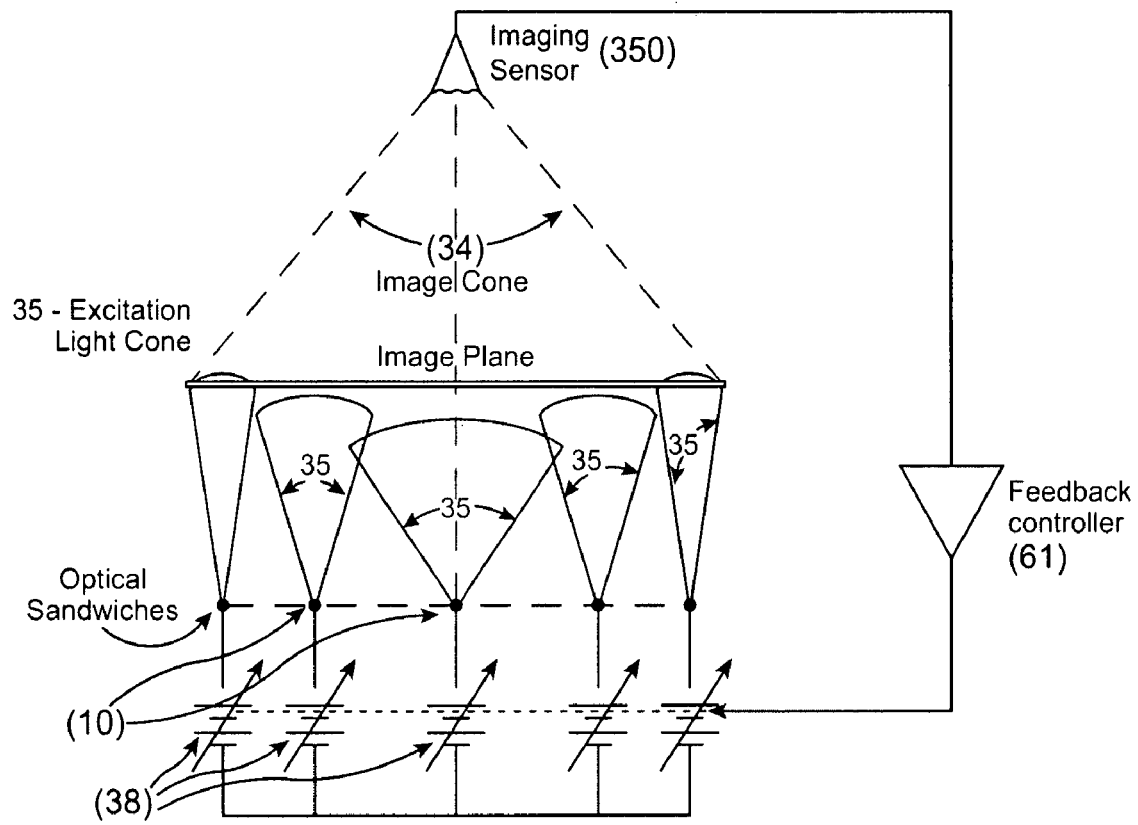
FIGS. 6A and 6B schematically show how the current, dispersion angle, and spacing of individual excitation sandwiches affect the excitation intensity on the image plane.
Figure 6B:
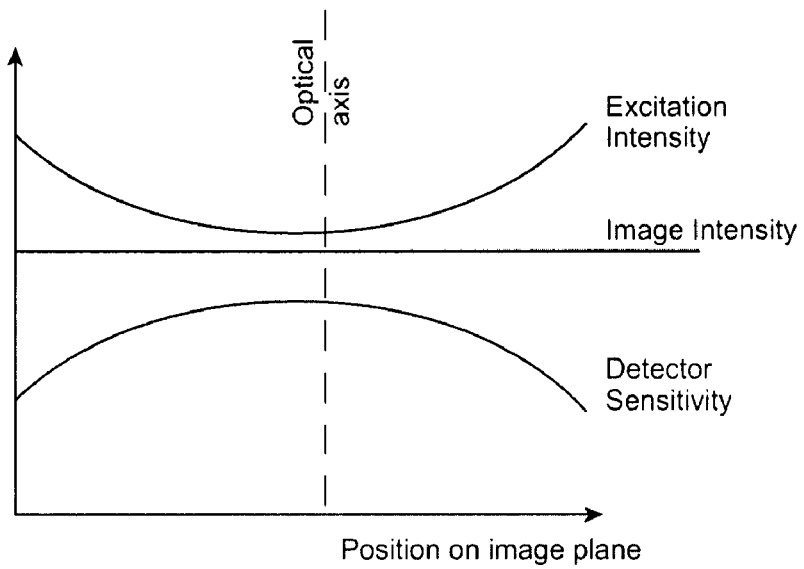

When a plurality of optical sandwiches is used to illuminate the sample, the light sources can be independently controlled to vary brightness, spacing and diffusion angles of several discrete sandwich assemblies as described above to achieve uniform sample illumination or uniform detection sensitivity. This invention also provides a remote control and optionally feedback control mechanism to vary and modify the brightness of individual light sources. FIGS. 6A and B schematically show how the current (38), dispersion angle of the excitation light cone (35), and spacing of individual excitation sandwiches (10) affect the excitation intensity on the image plane. Narrower dispersion, closer spacing, and higher current for the optical sandwiches at the edges result in brighter excitation at the edges. When convolved with lower edge sensitivity of the detector, the result is a more uniform image intensity from a uniform sample. An optional feedback controller (61) comprising the detector electronics and computer interface, image analysis software, and computer controlled programmable power supply for the excitation currents, automates adjustment and calibration of the excitation source currents. For simplicity, FIG. 6A shows a 1-dimensional image plane and the detector positioned above the image plane. In the actual apparatus, the detector is positioned below a 2-dimensional image plane. Also for simplicity the detector sensitivity and excitation intensity profiles shown are circular (FIG. 6B), but in practice they can be more complex spatial functions, and the feedback compensates for the functional form and its nonlinearities. The methodology of normalizing the variable light source and the detector is described below.

More uniformity can be achieved at any angle of illumination between the optical axis of the sandwich and the plane of the sample (θ in FIG. 5), for example between about 30 and about 70 degrees, or alternatively between about 35 and about 70 degrees, or alternatively between about 45 and about 60 degrees, or alternatively, between about 50 and about 60 degrees, or alternatively, greater than about 30 degrees, or alternatively less than about 70 degrees, or alternatively, less than about 60 degrees.

When the plurality of arrays are coupled to, or positioned on, a rotating shaft (see FIG. 3A), the number of arrays on the shaft can be 1 or 2, 3 or 4 or any integral amount up to an including 10 or more. For the purpose of illustration only, FIG. 3A shows 3 individual arrays (52), (54), and (56) each emitting light of a different color. The arrays are connected to a suitable actuator, which in FIG. 3A includes a high speed motor (58), a shaft (60) and coupler which rotates the arrays towards the sample receiving device. FIG. 3B shows a plurality of rotating shafts within an apparatus of this invention which is described in more detail below.

The rotating shaft allows use of alternate light sources and therefore wavelengths and intensities. As noted above, a particular embodiment is to place multiple monochromatic linear arrays of multiple wavelengths on the rotating shaft (See FIG. 3B (60)). In a further aspect, the shaft can be remotely controlled by a computer or other controller device. In a further aspect, multiple shafts can be synchronized to provide uniform illumination of the sample. The net effect is that by rotating the shaft, one can switch rapidly (<1 second) from one color to another of spectrally pure, spatially uniform light. This contrasts to some previously described devices wherein two different colored light sources (i.e., wavelengths) are rigidly placed next to each other, so both are not likely at their optimal geometrical positions.

In sum, the previous description of the various embodiments, while comprising varied components all can achieve spatial uniformity or an intentional non-uniform spatial profile of the excitation light (to complement a spatially non-uniform detector sensitivity profile, see below) by 1) varying the spacing and positions of the individual sandwiches in the array(s); 2) varying the current and brightness of individual light sources in the sandwiches; 3) varying the choice of diffusers or diffusion angle; and 4) as described in more detail below, the optional use of feedback control from the detector system to automatically adjust the individual light source currents (FIG. 6).

The Apparatus

The arrays of sandwiches and multiplicity of arrays described above can be incorporated into a fluidics and detection system for high throughput analysis of sample prepared for fluorescent and/or luminescent analysis. When incorporated into the detection system (exemplified in FIG. 5), the optical sandwich is combined with a device for receiving a sample container (31) and an imaging sensor (350) capable of detection of fluorescent and luminescent signals emitted from at least one of the plurality of the samples contained within the sample container or containers (31). The excitation light source, (20), (50), or (52), within the apparatus can be positioned either above, below or to the side of the sample container, or in any combination of above, below or to the side of the sample container or containers to produce the required illumination (33) covering the surface of the sample container or containers.

The Samples and Sample Container Receiving Device: In one aspect, the sample container receiving element (31) is situated below the head of an automated mutichannel pipettor, which includes, but is not limited to for example a Beckman Multimek or Velocity11 Bravo, in such a manner that the pipettor's fluidics functions can operate independently and concurrently with illumination and detection. This enables the apparatus to record optical responses to the addition of compounds, buffers, ligands, or other reagents. Sequential images taken before, during, and after fluidic additions reveal temporal kinetics of the sample's responses.

The sample is contained within one or more sample containers which in turn is held in a sample container receiving element supported by a stage. The sample can include compounds, mixtures, surfaces, solutions, emulsions, suspensions, cell cultures, fermentation cultures, cells, tissues, secretions, and/or derivatives and/or extracts thereof. Analysis of the compositions may involve measuring the presence, concentration, or physical properties of a luminescent and/or fluorescently labeled analyte in the sample. The sample container can include microplates, gene chips, or any array of samples such as microtiter plate or a plurality of microtiter plates for holding samples or compositions. The sample can comprise a single cell, a cell culture of the same cell type (clonal population) or a mixture of cells (including for example tissue samples obtained from a biopsy) or a subject or patient. Although the below examples utilize a multi-well plate for positioning and holding the sample in the device, the invention is not to be limited to detection of cells in an array. The sample receiving device also can hold a slide, an agar gel or a cuvette.

The sample must be suitably labeled for luminescent and/or fluorescent detection. Examples of luminescent labels that produce signals that can be detected using the device of this invention include, but are not limited to bioluminescence and chemiluminescence. Detectable luminescence response generally comprises a change in, or an occurrence of, a luminescence signal. Suitable methods and luminophores for luminescently labeling assay components are known in the art and described for example in Richard P. Haugland, Handbook of Fluorescent Probes and Research Chemicals (6$^{th}$ ed. 1996). Examples of luminescent probes include, but are not limited to, aequorin and luciferases.

The samples also can be labeled with a fluorescent label. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland (1996), supra.

In another aspect, the fluorescent label is functionalized to facilitate covalent attachment to a cellular component present in or on the surface of the cell or tissue such as a cell surface marker. Suitable functional groups, including, but not are limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

Attachment of the fluorescent label may be either directly to the cellular component or compound or alternatively, can by via a linker. Suitable binding pairs for use in indirectly linking the fluorescent label to the intermediate include, but are not limited to, antigens/antibodies, e.g., rhodamine/anti-rhodamine, biotin/avidin and biotin/strepavidin.

Figure 5:
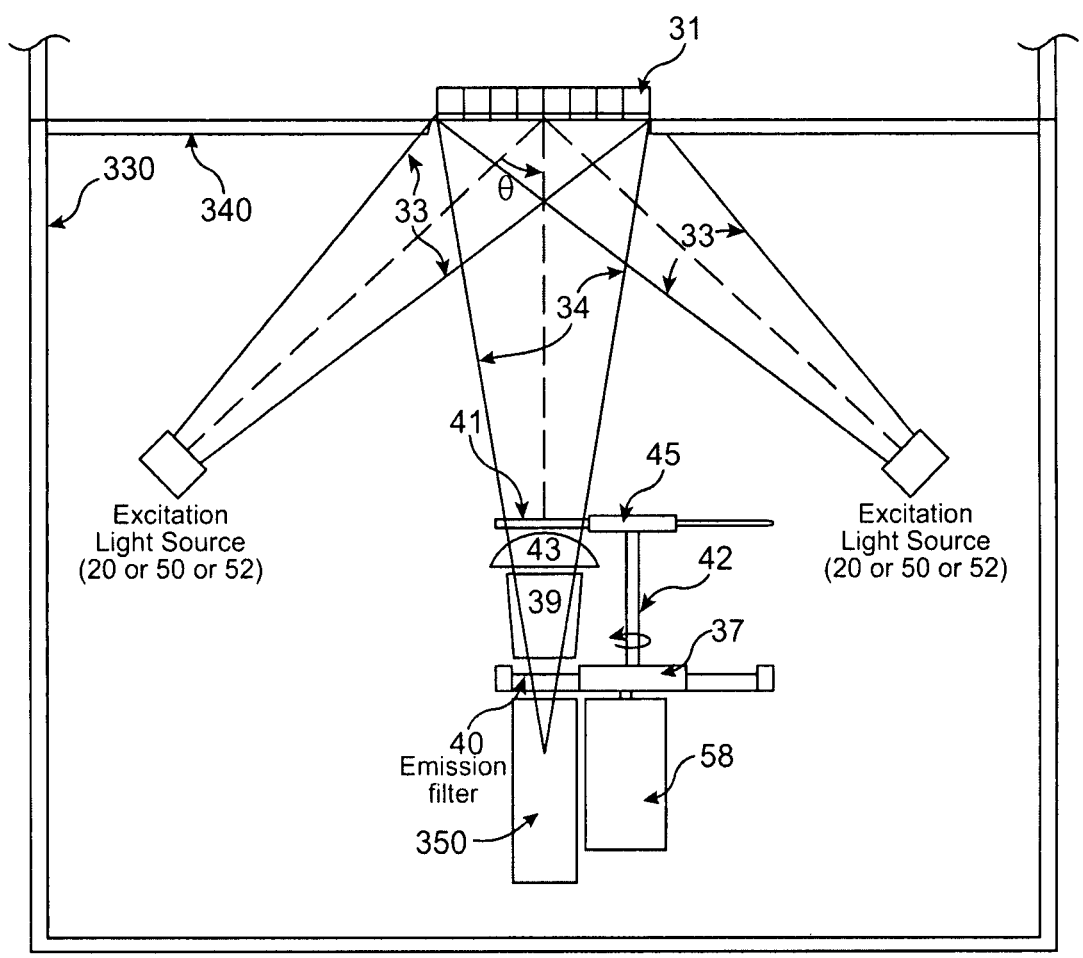
FIG. 5 shows the device and the varying positions of an emission filter wheel within the apparatus.

The Detector System: The apparatus of this invention also includes a detector system for imaging fluorescent or luminescent signal emitted from the samples. Referring to FIG. 5, the detector system comprises a detector lens (39), an emission filter (40) or (41), and an imaging sensor (350). An optional aspect comprises a close-up (43) to focus and magnify the image.

As used herein, the term "detector system" intends any device capable of converting energy from detected light into signals that may be transmitted to and processed by subsequent devices, such as a computer. Suitable detectors systems include photomultiplier imaging tubes, photodiodes arrays, avalanche photodiode arrays, charge-coupled devices (CCDs), and intensified CCDs (ICCDs), electron multiplying CCD (EMCCD), electron bombardment CDD (EBCCD), complementary metal oxide semiconductor (CMOS) imager, photomultiplier tube (PMT) arrays. These are commercially available from sources including Roper Scientific, Andor, Hamamatsu, and others. Depending on the detector system and assay mode, such detector lens may be used in photon-counting or integrating modes. The apparatus can optionally contain more than one type of detector system for multimode reading and subsequent analysis.

The detector system also contains an emission filter ((40) or (41)). Examples of suitable emission filters include, but are not limited to optical filters, tunable filters, acetate filters and interference filters. These filters are commercially available from sources including Semrock, Omega, Chroma, and others. In luminescence modes, an emission filter can be used to select from multiplexed luminophores emitting in different colors, and it also can block infrared emissions from nearby apparatus. In fluorescence modes, the emission filters block excitation wavelengths from the detector. The excitation light is generally many orders of magnitude brighter than the fluorescence emission from the sample, requiring attenuation to not contaminate the fluorescence emission. The angles of incidence of the light sources are schematically shown in FIG. 5 (33 and θ) along with the image cone (34) of the detector system.

In another aspect, the emission filter is positioned on a rotating filter wheel to filter emission produced by the samples. In one aspect, the rotating filter wheel can be optionally programmable. For example, in the assembly shown in FIG. 5, a programmable rotating filter wheel ((37) or (45)) positions emission filters both above and below the detector lens that may be connected by a shaft (42). Positioning the emission filter in front of the detector lens has the advantage that it blocks excitation light from entering the lens and potentially exciting fluorescence of the optical elements. Positioning the emission filter behind the detector lens has the advantage of enabling a smaller diameter filter. Positioning emission filters in both positions offers the advantage of nearly squaring the filter's transmission efficiency, because the positions are far enough apart for the light to decohere. For example, if an emission filter has a 90% passband transmission and $10^{-5}$ stopband transmission then the two filters should have close to 80% passband transmission and $10^{-10}$ stopband. Either or both filter positions can be used as alternative embodiments.

The detector system also includes a detector lens (39). Examples of suitable detector lens include, but are not limited to photographic or imaging quality lenses, telecentric lenses and video lenses, which are commercially available from Nikon, Edmund Optical, Zeiss, and others.

In one optional embodiment, the assembly may optionally include software and computer means to remotely controlling the lens aperture to maximize sensitivity towards bioluminescence and increase spectral and spatial fidelity for fluorescence.

In another optional embodiment, the detector system is remotely connected to at least one optical sandwich in the apparatus so that illumination and detection are synchronized. This avoids bleaching fluorophores while the detector is idle or detecting luminescence. It can be achieved by gating the excitation illumination with the detector shutter or other command signal to or from the detector.

Referring to FIG. 6, the detector can also provide feedback control (61) of the excitation intensity to optimize spatial uniformity. This can be achieved using a computer-controlled programmable power supply such as are commercially available from Agilent, Leader, and other vendors. The feedback control can compensate for spatial non-uniformity in any combination of the detector, the optical system, and the sample. A set of images from the detector are obtained while changing the current (and intensity) of individual light sources such as LEDs. The resulting images are analyzed and the effects of the current changes on the brightness and uniformity are inferred. The software can be used to predict and set the individual LEDs to achieve the desired combination of brightness and uniformity across the entire sample. FIG. 7 illustrates this aspect.

Figure 7B:
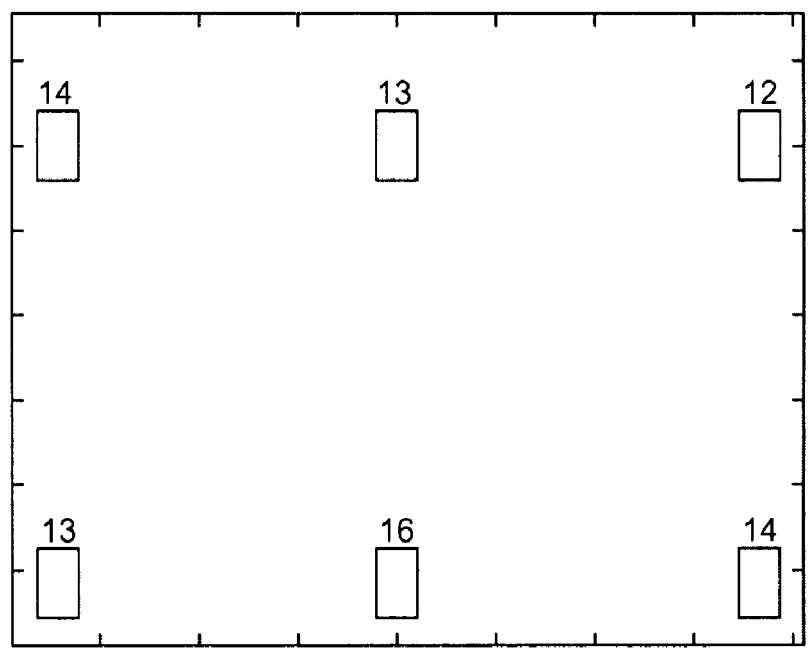
FIGS. 7A and 7B demonstrate how feedback from the detector can be used to reduce spatial variability of the excitation light.
Figure 7A:
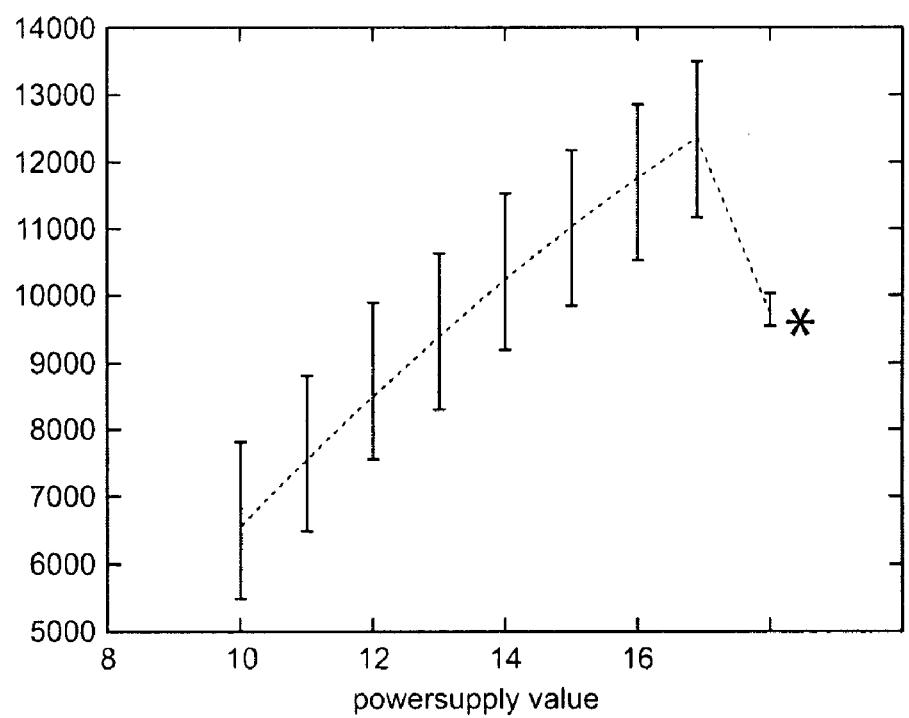

Six (6) ultrabright LED dies were imaged at a range of intensities and feedback from the detector was used to reduce variability of the LED's brightness. FIG. 7A shows the mean and standard deviation of the 6 LED intensities detected by a CCD camera as the programmable power supply current for each LED was varied. X axis indicates power supply value from 10-17 (arbitrary units corresponding to about 25-50 mA). Upon software analysis of the images, the LED currents were individually set to predicted optimal values that achieved a uniform intensity around 10000 (arbitrary units of the camera). The results are the rightmost point (*), showing a ~5× increase in uniformity at the desired intensity. FIG. 7B shows the negative CCD image of the 6 LEDs with at the optimal power supply settings indicated numerically above the images of each die. X- and Y-axis correspond to horizontal and vertical position in the CCD image.

Figure 4:
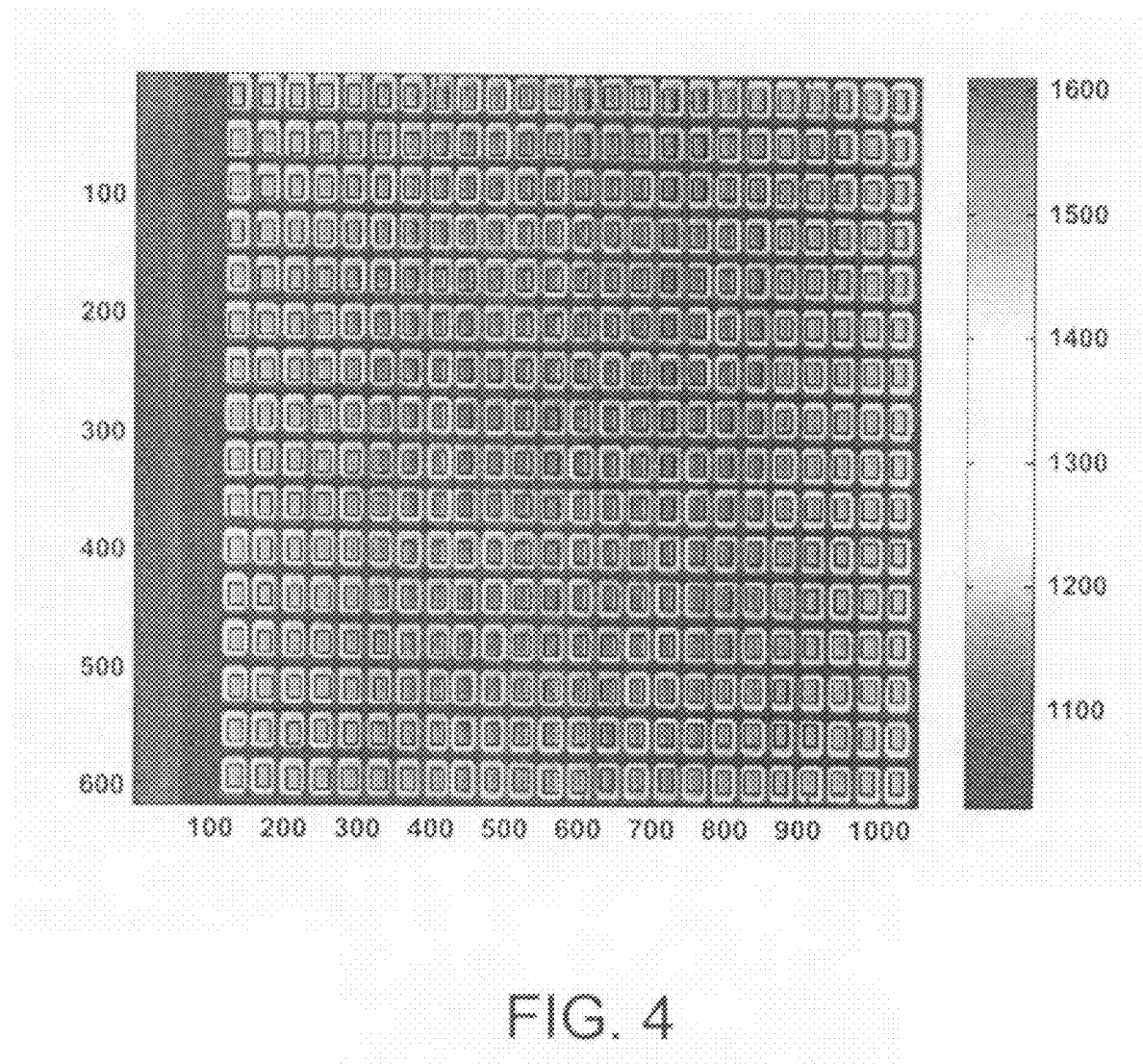
FIG. 4 shows the illumination pattern achieved with biased illumination through multiple LED light sources.

In practice in the apparatus, feedback is typically used in a similar manner to minimize variance across a uniform fluorescence reference plate. Results of this process are exemplified in FIG. 4, showing approximately 10% variability of integrated signal over each of the active wells.

In a yet further aspect, the imaging detector apparatus can optionally include a means or apparatus to remove condensation or fog from the sample container. Condensation often forms on the bottom of microtiter plates that are stacked on top of each other. Condensation or fog can obscure and degrade optical imaging through the transparent sample container bottom. This especially impairs fluorescence detection because the increased reflection and scattering of excitation light increases leakage through the emission filter. A fan, a heat source such as a heating element, heat lamp, or a mechanical wiper or a dehumidifier can be used to remove condensation or fog from the sample container.

It should be understood, without being explicitly stated that the apparatus of the invention optionally includes without limitation the variations and alternate embodiments present in each of the foregoing examples of the elements, e.g., the optical sandwiches, the arrays and the plurality of arrays. Thus, for example, the apparatus will, in one embodiment, contain a plurality of arrays on a rotating shaft with each array of sandwich elements emitting light of a different wavelength.

Screening System

Figure 9:
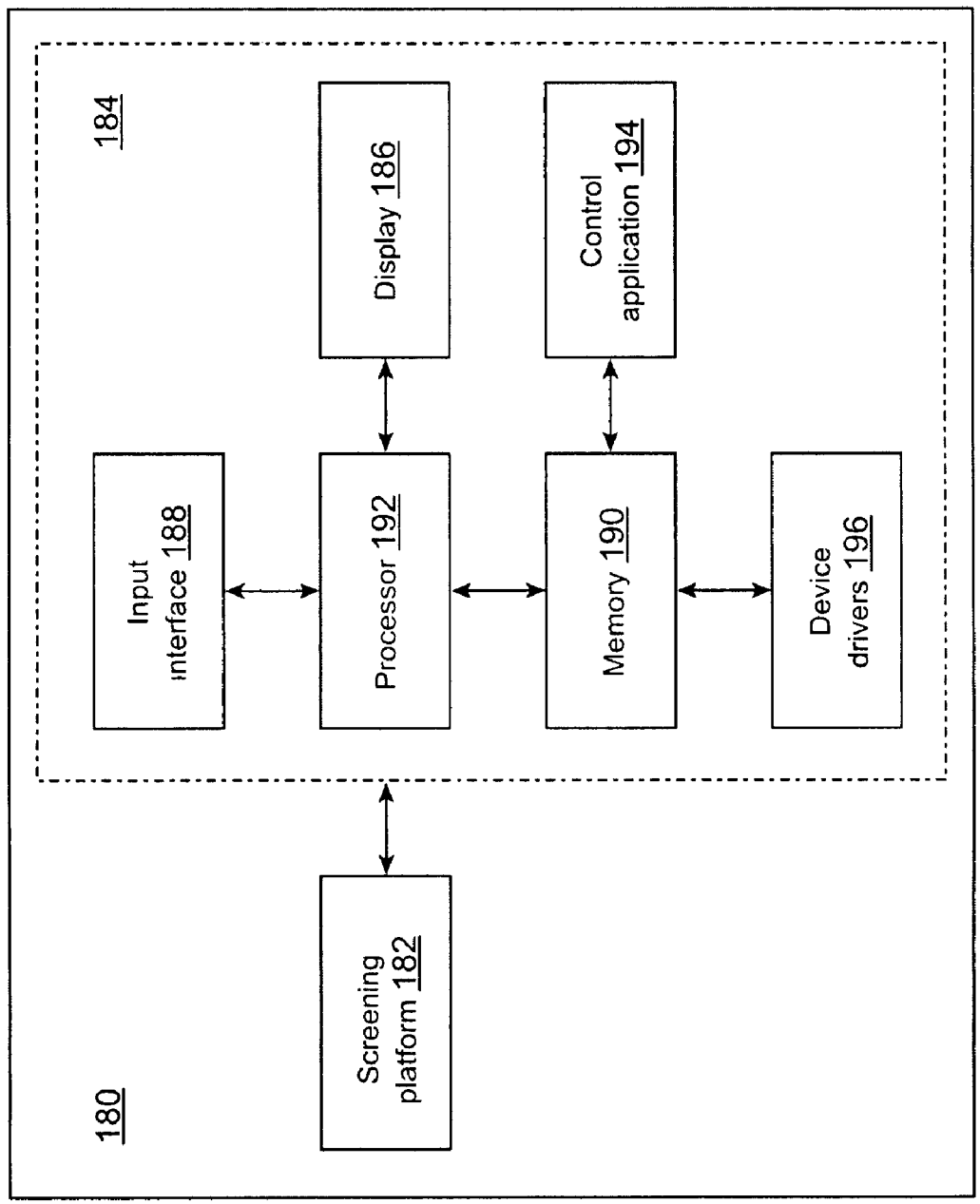
FIG. 9 depicts a block diagram of the screening system in accordance with an exemplary embodiment.

With reference to FIG. 9, a block diagram of a screening system (180) is shown in accordance with an exemplary embodiment. Screening system (180) may include a screening platform (182) and a controller (184). Controller (184) may include a display (186), an input interface (188), a memory (190), a processor (192), a control application (194), and one or more device drivers (196). Components of screening system (180) may be positioned in a single location and/or may be remote from one another. As a result, controller (184) may include a communication interface, which provides an interface for receiving and transmitting data between devices using various protocols, transmission technologies, and media as known to those skilled in the art. The communication interface may support communication using various transmission media that may be wired or wireless. Controller (184) may be a computer or computing device of any form factor.

In the embodiment illustrated in FIG. 9, screening platform (182) analyzes assays using an imaging plate reader with multi-channel pipetting capability. Screening platform (182) may include, but is not limited to, a stacker, an incubator, a robotic gripper, one or more optical assemblies, an automated multi-channel pipettor, a detector, etc. Controller (184) controls the operations of screening platform (182) using the one or more device drivers (196) and control application (194). In general, a device driver acts as a translator for a device associated with the device driver. Screening platform (182) includes the devices associated with the one or more device drivers (196).

Display (186) presents information to a user of controller (184) as known to those skilled in the art. For example, display (186) may be a thin film transistor display, a light emitting diode display, a liquid crystal display, or any of a variety of different displays known to those skilled in the art now or in the future.

Input interface (188) provides an interface for receiving information from the user for entry into controller (184) as known to those skilled in the art. Input interface (188) may use various input technologies including, but not limited to, a keyboard, a pen and touch screen, a mouse, a track ball, a touch screen, a keypad, one or more buttons, etc. to allow the user to enter information into controller (184) or to make selections presented in a user interface displayed on display (186). Input interface (188) may provide both an input and an output interface. For example, a touch screen both allows user input and presents output to the user.

Memory (190) is an electronic holding place or electronic storage for information so that the information can be accessed by processor (192) as known to those skilled in the art. Controller (184) may have one or more memories that use the same or a different memory technology. Memory technologies include, but are not limited to, any type of RAM, any type of ROM, any type of flash memory, etc. Controller (184) also may have one or more drives that support the loading of a memory media such as a compact disk or digital video disk.

Processor (192) executes instructions as known to those skilled in the art. The instructions may be carried out by a special purpose computer, logic circuits, or hardware circuits. Thus, processor (192) may be implemented in hardware, firmware, software, or any combination of these methods. The term "execution" is the process of running an application or the carrying out of the operation called for by an instruction. The instructions may be written using one or more programming language, scripting language, assembly language, etc. Processor (192) executes an instruction, meaning that it performs the operations called for by that instruction.

Processor (192) operably couples with display (186), with input interface (188), with memory (190), with screening platform (182), and with the communication interface to receive, to send, and to process information. Processor (192) may retrieve a set of instructions from a permanent memory device and copy the instructions in an executable form to a temporary memory device that is generally some form of RAM. Controller (184) may include a plurality of processors that use the same or a different processing technology. The one or more device drivers (196) and control application (194) may be executed by the same processor (192) or by different processors.

Each device has a set of specialized controls that its device driver understands and uses to communicate with the device. Control application (194) may not directly control one of the devices of screening platform (182). Instead, control application (194) may be implemented as a state machine integrated with a device driver of the one or more device drivers (196). Control application (194) performs operations associated with allowing a user to define a protocol for controlling an execution of screening platform (182). A protocol is a series of commands, operator(s), and/or expression(s) that represent a sequence of related actions to be performed by screening platform (182). A command is a call to one of the one or more device drivers (196).

The operations of control application (194) may be implemented using hardware, firmware, software, or any combination of these methods. With reference to the exemplary embodiment of FIG. 9, control application (194) is implemented in software stored in memory (190) and accessible by processor (192) for execution of the instructions that embody the operations of control application (194) and the operations of the protocol. Control application (194) may be written using one or more programming languages, assembly languages, scripting languages, etc.

The one or more device drivers (196) may be implemented using hardware, firmware, software, or any combination of these methods. With reference to the exemplary embodiment of FIG. 9, one or more device drivers (196) are implemented in software stored in memory (190) and accessible by processor (192) for execution of the instructions that embody the operations of one or more device drivers (196). The one or more device drivers (196) may be written using one or more programming languages, assembly languages, scripting languages, etc.

Figure 10:
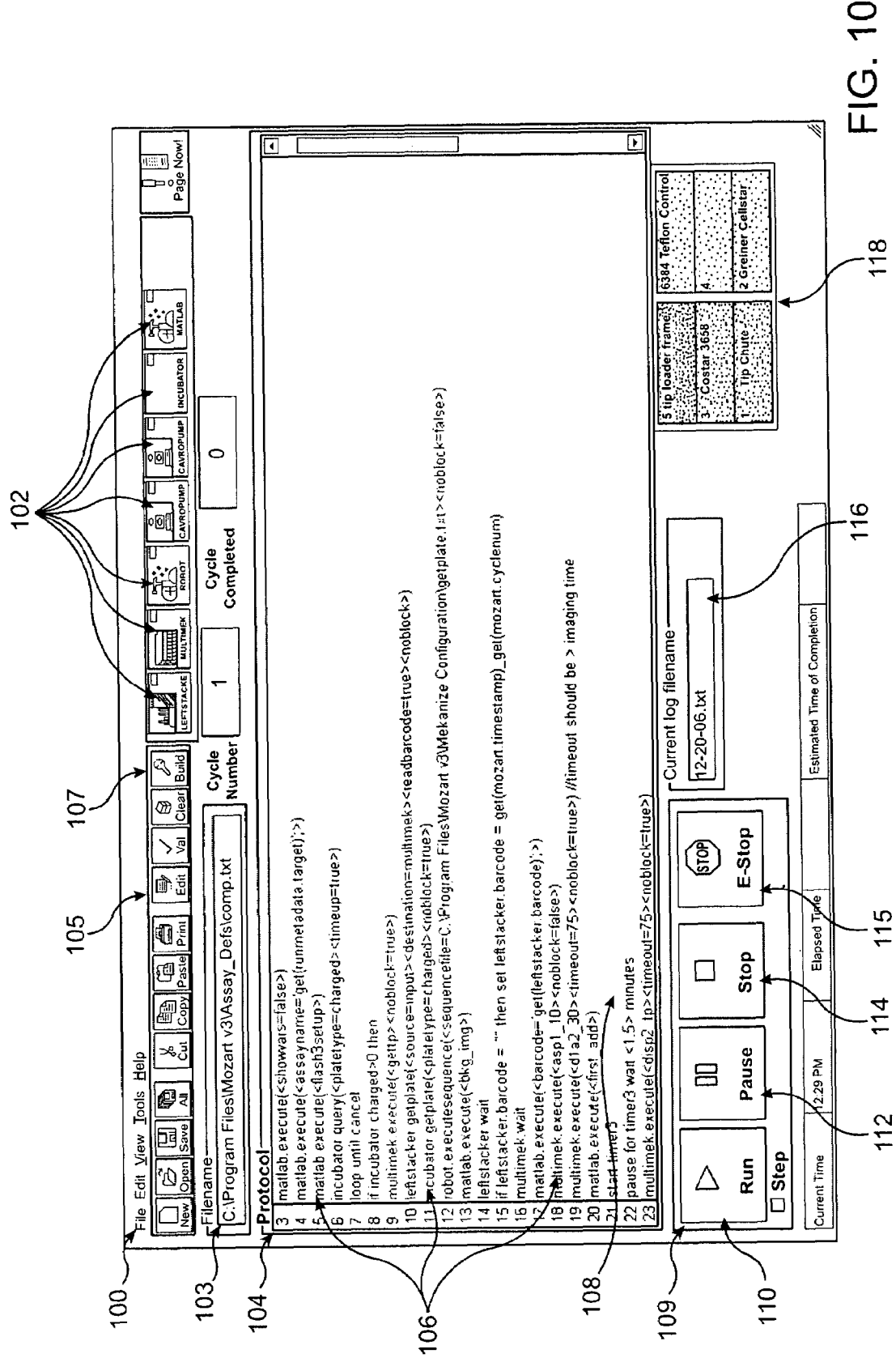
FIG. 10 depicts a user interface of a control application in accordance with an exemplary embodiment.

With reference to FIG. 10, a user interface (100) of control application (194) is shown. User interface (100) may include a plurality of device buttons (102), a protocol filename text box (103), a protocol window (104), an execution control area (109), a log filename text box (116), and a deck layout area (118). Protocol filename text box (103) includes the filename and path to the protocol selected for execution by the user. Log filename text box (116) includes the filename of the log file generated during execution of the protocol selected. For example, the log file may contain a storage location mapped to a bar code for a sample in addition to a time to support system recovery and development of a process history. As a result, no additional bar code labeler may be required as part of screening system (180). The time may include the date.

Protocol window (104) displays a plurality of command lines (106) of the protocol selected for execution by the user. Each command line may include a command, an operator, an expression, a comment, etc. Protocol window (104) optionally may display the protocol without allowing editing of the protocol. Additionally, or in the alternative, protocol window (104) may display the protocol and allow editing of the protocol. For example, user selection of an edit button (105) may allow the user to edit the protocol displayed in protocol window (104). User selection of a build button (107) allows the user to build the protocol displayed in protocol window (104) with the device drivers associated with devices selected from the plurality of device buttons (102).

Control area (109) may include a plurality of buttons that allow the user to control execution of the protocol. In the exemplary embodiment of FIG. 10, control area (109) includes a run button (110), a pause button (112), a stop button (114), and an emergency stop button (115). Run button (110) starts execution of the protocol. Pause button (112) pauses execution of the protocol. Stop button (114) stops execution of the protocol at the completion of the currently executing command. Emergency stop button (115) stops execution of the protocol immediately.

Deck layout area (118) provides control application (see FIG. 9, (194)) with information related to the type of labware included as part of screening platform (182). The associated labware definition informs the system of pipetting parameters such as aspiration and dispense height, volume limits, geometric limitations, etc. For example, geometric limitations may be utilized for collision avoidance.

Figure 11:
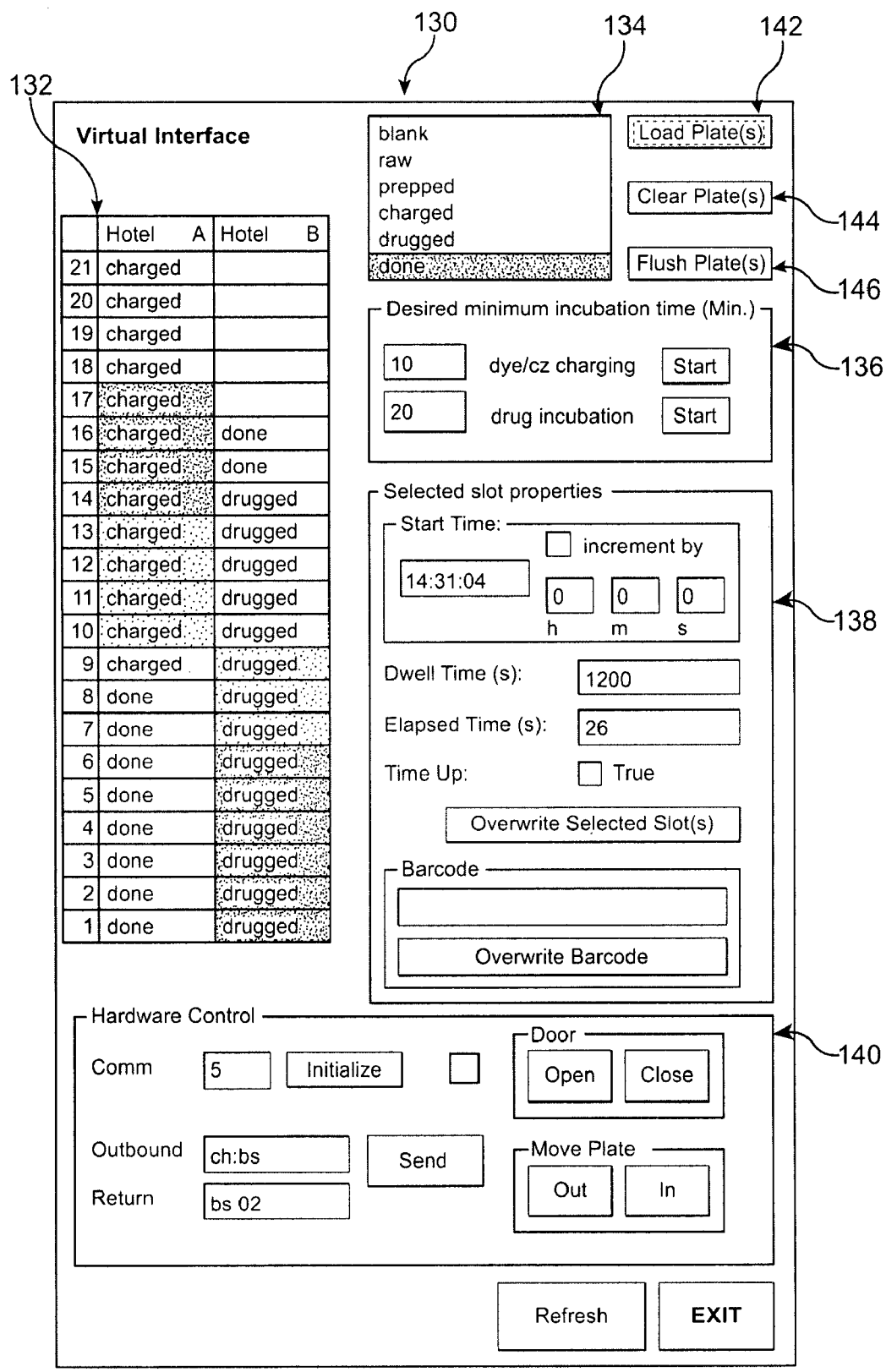
FIG. 11 depicts a user interface of a device driver in accordance with an exemplary embodiment.

With reference to FIG. 11, a user interface (130) of an exemplary device driver is shown. In the exemplary embodiment of FIG. 11, the device driver is for an incubator that allows tracking of individual plate properties such as a type of process, a bar code, and incubation parameters. User interface (130) may include a virtual plate interface (VI) (132), category selector (134), an incubation timing area (136), a slot property area (138), and a hardware control area (140). VI (132) depicts storage layout of the incubator and represents the contents of the incubator. A user can use the mouse to select the slots where plates have been loaded and select an item from category selector (134) to choose a plate category. Exemplary categories include: raw=blank=prepped, which indicates cell plates that have not been loaded with charging agents or which are placeholders; charged, which indicates cell plates loaded with coelenterazine or dye; drugged, which indicates cell plates loaded with compounds; done, which indicates cell plates processed with no further operation needed. A user can select a "load plate" action button (142) to set the plates into VI (132). Similarly, selected plates can be manually cleared off VI (132) by selecting a "clear plate" action button (144). A "flush plate" action button (146) is used to force a current state of the selected plates into readiness (i.e., green). User interface (130) may remain interactive throughout the execution of an assay. Thus, a user can control the assay execution, if so desired, by changing the plate categories manually using user interface (130) thereby setting or overriding a current state.

Incubation timing area (136) allows the user to manually set incubation time prior to assay execution, although this is generally automated using a protocol script. Using controls of incubation timing area (136), the user can enter the minutes of desired time for the dye/coelenterazine charging and drug incubation, select the targeted plates in VI (132), and select a "start" button to initiate a timer. VI (132) reflects the readiness of the plates continuously and initiate processes upon satisfaction of incubation requirements defined by the user. Colors on VI (132) may indicate the state of the cell plates. For example, green may indicate that a plate is ready to process, red may indicate that a plate is incubating, and no color may indicate that a plate is done or waiting for manual time setting by the user. Each position (or slot) of VI (132) holds these properties: StartTime, ElapseTime, DwellTime, PlateType, TimeUp, and Barcode, which can be recorded in a log file for error recovery.

Slot property area (138) allows the user to modify selected slot properties, if so desired, such as the StartTime, ElapseTime, DwellTime, TimeUp, and Barcode. Hardware control area (140) provides a hardware control interface for diagnostic access to the incubator.

Each device has a set of commands with associated command properties that may be defined by a user of control application (see FIG. 9 (194)). The commands and properties differ for each type of device. Control application (194) implements a state engine that interacts with a device driver to control processing flow for a screening process. For example, a protocol queries a plate status in the incubator and chooses the next process for execution based on the status returned from the query. An exemplary protocol shown below illustrates use of the state engine:

```
[PROTOCOL]
incubator.query(<platetype=drugged><timeup=true>)
matlab.execute(<assayname='get(runmetadata.target)';>)
matlab.execute(<flash3setup>)
set mozart.tips = 0
loop until cancel
// process a drugged plate, i.e., compound incubated cell plate, capture kinetics imaging
if incubator.drugged > 0 then
    if get(mozart.tips) = 0 then multimek.execute(<gettp><noblock=true>)
    set mozart.tips = 1
    incubator.getplate(<platetype=drugged><timeup=true><getbarcode=true><noblock=true>)
    incubator.wait(<type=get>)
    robot.executesequence(<sequencefile=C:\Program Files\Mozart v3\Mekanize
        Configuration\getplate.txt><noblock=false>)
    if incubator.barcode = "" then
        promptforbarcode
        set incubator.barcode = get(user.barcode)
        msgbox "You can also prefill barcode in the Incubator driver to skip this manual step"
    end if
//load data from 1st addition imaging
    matlab.execute(<barcode='get(incubator.barcode)';load_data;>)
    multimek.wait
    multimek.execute(<asp2_30>)
    multimek.execute(<disp2><timeout=75><noblock=true>)
    matlab.execute(<second_add>)
    matlab.execute(<save_second>)
    robot.executesequence(<sequencefile=C:\Program Files\Mozart v3\Mekanize
        Configuration\returnplate.txt><noblock=false>)
    incubator.returnplate(<platetype=done><barcode=get(matlab.barcode)><noblock=true>)
    multimek.wait
end if
incubator.query(<platetype=drugged><timeup=true>)
if incubator.drugged < 1 then
    incubator.query(<platetype=charged><timeup=true>)
    //process a charged plate, i.e., cz/dye loaded cell plate, for compound addition and capture kinetics
    //imaging followed by incubation to become "drugged" plate
    if incubator.charged > 0 then
        if get(mozart.tips) = 1 then multimek.execute(<trstp>)
        multimek.execute(<gettp><noblock=true>)
        set mozart.tips = 1
        leftstacker.getplate(<source=input><destination=multimek><readbarcode=true><noblock>)
        incubator.getplate(<platetype=charged><noblock=true>)
        incubator.wait(<type=get>)
        robot.executesequence(<sequencefile=C:\Program Files\Mozart v3\Mekanize
            Configuration\getplate.txt><noblock=false>)
        matlab.execute(<bkg_img>)
        leftstacker.wait
        if leftstacker.barcode = "" then set leftstacker.barcode =
            get(mozart.timestamp)_get(mozart.cyclenum)
        multimek.wait
        matlab.execute(<barcode='get(leftstacker.barcode)';>)
        multimek.execute(<asp1_10><noblock=false>)
        multimek.execute(<disp1_tp><timeout=180><noblock=true>)
        set mozart.tips = 0
        matlab.execute(<first_add>)
        matlab.execute(<save_first>)
        robot.executesequence(<sequencefile=C:\Program Files\Mozart v3\Mekanize
            Configuration\returnplate.txt><noblock=true>)
        multimek.wait
        matlab.execute(<returnvar=barcode>)
        matlab.execute(<clear barcode>)
        incubator.returnplate(<platetype=drugged><dwelltime=1800><barcode=get(matlab.barcode)>
            <noblock=true>)
        leftstacker.returnplate(<source=multimek><destination=output><noblock=false>)
    end if
    //determine if there is anything else to do
    if incubator.charged = 0 then
        if incubator.drugged = 0 then
            incubator.waituntil(<timeup=true>)
            if incubator.todo = 0 then
                if get(mozart.tips) = 1 then multimek.execute(<trstp>)
                set mozart.tips = 0
                exit loop
            end if
        end if
    end if
end if
end loop
```

Figure 12:
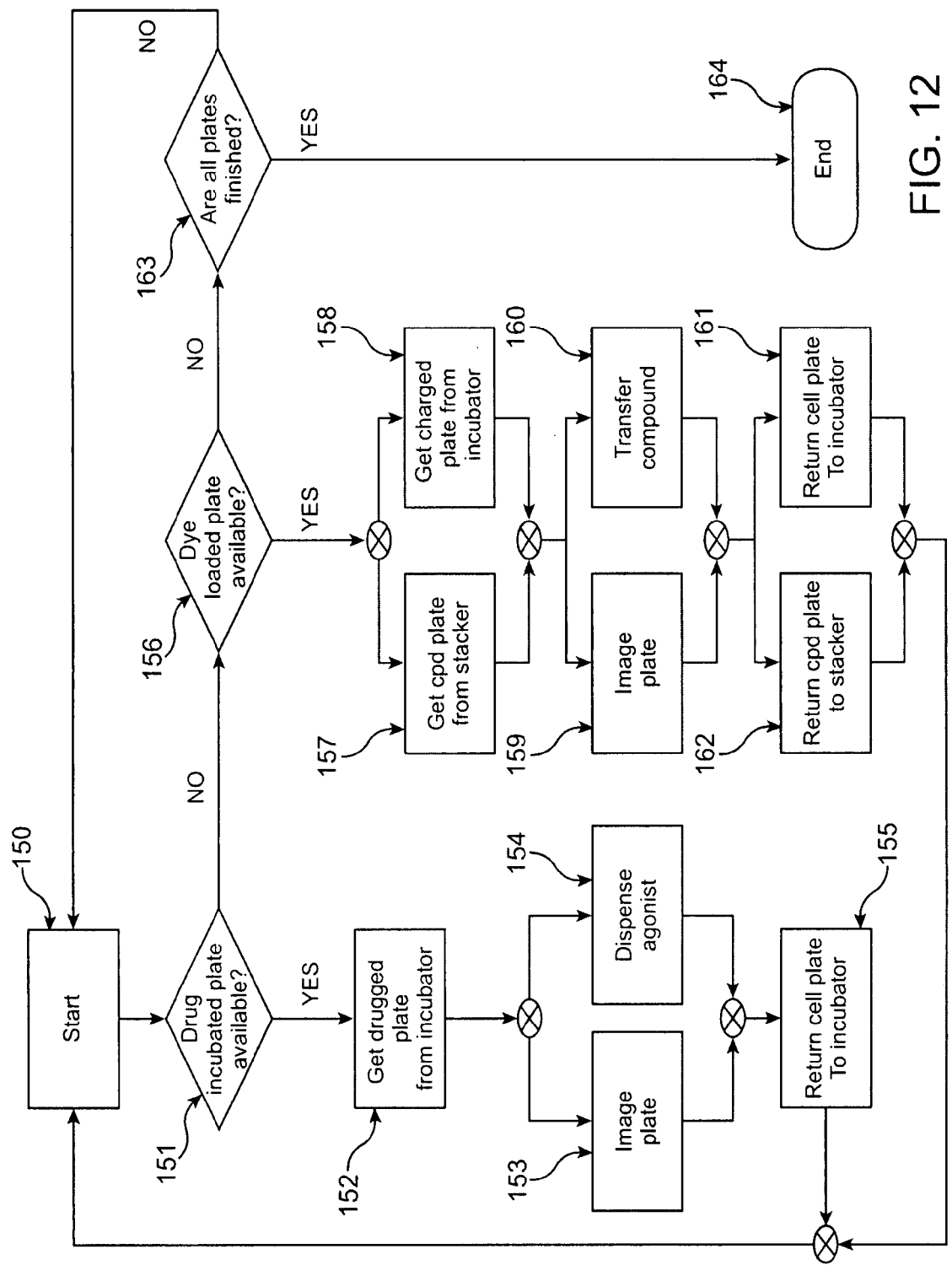
FIG. 12 depicts exemplary operations of a screening process in accordance with an exemplary embodiment.

The protocol shown above executes the screening process indicated in the flow chart of FIG. 12. Additional, fewer, or different operations may be performed, depending on the screening process to be executed. In an operation (150), a screening process is started for example by querying if any drugged plate is currently available to be processed. In an operation (151), a determination of whether or not a plate of screening platform (182) is drugged is performed. If a plate is drugged, processing continues at an operation (152). If no plate is drugged, processing continues at an operation (156). In an operation (152), the drug incubated cell plate (drugged plate) is moved from an incubator to an imaging plate reader. In an operation (153), the drugged plate is imaged. In an operation (154), an agonist or activation reagent is dispensed onto the drugged plate. Performance of operations (153) and (154) are controlled by the order of execution of the commands and the timing properties provided with the commands. Generally the two operations are simultaneous. In an operation (155), the drugged plate is moved from the imaging plate reader to the incubator and its state is changed to "done", or alternatively, discarded. The process then returns to (150) in which another query for drugged plates is issued and determination is made at (151).

If the determination at (151) is negative, the screening process is continued for example by querying if any charged plate is currently available. In an operation (156), a determination of whether or not a plate of screening platform (182) is charged or loaded with a dye is performed. If a plate is charged, processing continues at an operation (157) and at an operation (158). If no plate is charged, processing continues at an operation (163). In operation (157), the compound plate is moved from a plate storage device, i.e., a stacker, to the deck of imaging plate reader. In operation (158), the charged cell plate is moved from the incubator to the imaging location on the imaging plate reader. In an operation (159), the charged cell plate is imaged. In an operation (160), drug is transferred from the compound plate and dispensed onto the charged cell plate. Performance of operations (159) and (160) are controlled by the order of execution of the commands and the timing properties provided with the commands. Generally the two operations are simultaneous. In an operation (161), the charged cell plate is moved from the imaging plate reader to the incubator and its state is changed to "drugged". In an operation (162), the compound plate is moved from the imaging plate reader to the stacker. Performance of operations (161) and (162) are controlled by the order of execution of the commands and the timing properties provided with the commands.

In an operation (163), a query determines if all plates of screening platform (182) have been processed. If all plates of screening platform (182) have been processed, processing stops at an operation (164). If all plates of screening platform (182) have not been processed, processing continues at operation (150).

By changing the order of execution of the commands executed for a given state and/or properties of the commands, the user can create a variety of screening processes. Through use of the state engine which queries for a status and determines the next process based on the status, control application (194) provides the flexibility of a dynamic scheduler without the complexity and overhead associated with a dynamic scheduler.

Use of the Assembly and/or Apparatus

Due in part to the uniqueness of the optical sandwich, the excitation source provides the spatially uniform and spectrally pure excitation source with minimal mechanical components. Thus, the assembly provides the substantially uniform excitation source without the use of a mirror array. It also does not require complex illumination geometry to minimize background fluorescence and interference (see U.S. Pat. No. 6,985,225).

Another advantage of this assembly is the flexibility and variability of the arrangement of the excitation sources. The excitation source can be comprised of one or more sandwiches that can be located in various positions around the sample. Any currently available sources can be utilized in the assembly. The light sources can be of unequal intensity, each source can be biased with a specific current thereby individually controlling their intensities. Uniformity can be achieved by feedback control with a reference plate. Use of unequal intensity through more than one light source can achieve a more uniform fluorescence over a multiwell plate (see FIG. 4).

A unique advantage provided by this apparatus is the ability to interleave concurrent fluorescence and bioluminescence imaging. This is possible because of the following:

1) Fluorophores don't contaminate the luminescence signal. Fluorophore concentrations are typically such that detecting a fluorescence signal requires a relatively enormous excitation flux, many orders of magnitude brighter than the typical luminescence flux. Insignificant perturbations of a few photons might occur by dye or quencher molecules absorbing a luminescent photon, but most such molecules are above the cell layer on the plate bottom, and only downward directed photons would reach the detector anyway. This minor absorptive effect should be offset by a few upward-directed luminescent photons exciting a fluorophore that reemits toward the detector (which is agnostic to color in luminescence mode). The dye (with the LED excitation turned off) therefore does not significantly modulate the bioluminescence signal. The blue LEDs can turn on and off with a time constant ~100 nsec, and exhibit no significant phosfluorescence or afterglow when power is removed.

2) Bioluminescence won't contaminate the fluorescence signal. The LEDs are bright enough and the camera sensitive enough that fluorescence can be measured within <~100 msec with typical fluorophore staining levels and cell densities. During such a short exposure, emitted bioluminescence signal is insignificant (e.g., aequorin exposures are typically a few seconds). Secondly, most aequorin emission is at blue wavelengths that are blocked by the typical longer wavelength emission filters.

3) Bioluminescence and fluorescence can be alternately imaged with little loss in either channel. Alternating a ~100 msec fluorescence exposure with a few second bioluminescence exposure provides two independent concurrent data streams with minimal loss compared to measuring either signal by itself. During ~200 msec that the camera requires to read-out the image, the emission filters are rotated selecting either aequorin or fluorescence sensitivity. The luminescence exposure of a few seconds must be reduced by <~10% to accommodate a brief fluorescence image. This is generally insignificant (and could generally be compensated if necessary with additional cell density and/or coelenterazine. Additional color emission filters (and LED banks) could be rotated into place for detecting additional spectral channels, each inducing an additional loss of aequorin sensitivity ~10%. Concurrent bioluminescence requires that fluorescence signal be acquired at a much lower frame rate than possible in dedicated fluorescence mode, however most common fluorophores used in screening exhibit pharmacological kinetics with time constants of seconds (and longer) so this limitation is not significant.

4) The wide dynamic range of a chilled CCD sensor with short (i.e., less than ½ second) readout, a very dark enclosure, and high optical and spectral fidelity inherent in our apparatus.

The interleaved detection of fluorescence and luminescence timing is illustrated in the timing diagram of FIG. 1. During each interval of a few seconds, multiple images are taken for two fluorescent colors and bioluminescence. Relative timing of each exposure, emission filter wheel rotation, and camera read-out are shown. Readout is required between exposures to dump the images from a detection system to a computer. Short readout and fluorescence exposures result in only a nominal loss of bioluminescence exposure which occupies most of the interval.

In summary, a short fluorescent exposure can be interleaved with a luminescence exposure, resulting in independent data in both luminescence and fluorescence channels, with only a nominal loss (i.e., less than 20%) of luminescent signal. Multiple color fluorescence exposures can also be obtained with nominal additional loss of luminescence signal enabling additional information to be concurrently measured.

Interleaving measurement of fluorescence and bioluminescence make it possible to simultaneously measure for example, membrane potential and intracellular calcium concentrations in cell populations contained in 384 well plates. This information would be highly valuable in ascertaining the pharmacology and mechanism of action of compounds on their targets. At a very modest cost of fluorophore and an insignificant ~10% sensitivity loss, such information would be available upon executing the screen and not after time- and resource-consuming follow-up tests. Fewer compounds would need to be reordered for confirmation and validation, and more quality data would be available significantly sooner.

The present invention also relates to a method for interleaving detection of fluorescent and luminescent signals emitted from a plurality of samples, which involves detecting fluorescent and luminescent signals produced by the plurality of samples. The fluorescence excitation light source is automatically turned off or shuttered during interleaved luminescence imaging. The method can be practiced using the apparatus of the present invention. Alternatively, a different apparatus, examples of which are commercially available, could achieve this functionality, if suitably modified. For example, a Molecular Devices FLIPR Tetra, CyBio Lumax, Perkin-Elmer CellLux or Lumilux, Hamamatsu FDSS, or other dispense-and-image plate readers existing now or in the future, might achieve interleaved imaging of fluorescence and bioluminescence by any of the following modifications: 1) more tightly sealing the enclosure to reduce light leaks; 2) baffling, covering, or eliminating internal infrared or visible (non-excitation) light sources; 3) installing a more sensitive (e.g, backthinned) CCD detector; 4) installation of enabling software; 5) installing a fast-switching emission filter; 6) addition of a spectrally pure, spatially uniform excitation light source; or other changes.

Experimental Examples

The following examples are intended to illustrate various embodiments of screening system (see FIG. 9 (180)) and in particular, its utility for high throughput agonist and antagonist drug screening in 384 well plates. The kinetic responses to multiple compound dilutions further suggest compound pharmacology and mechanism of action.

Samples were prepared as follows. Chinese Hamster Ovary Cells (CHO) endogenously express a G-protein coupled receptor (GPCR) that responds to purinergic compounds such as adenosine triphosphate (ATP) by increasing cytoplasmic calcium concentration. Cells were transfected and selected for stable expression of the apo-aequorin gene, which forms a bioluminescence complex sensitive to intracellular calcium (e.g., Cobbold P H et al. (1983), J Cell Sci 61:123-136; Shimomura 0 & Shimomura A, (1984), Biochem J. 228:745-9). CHO cells were thawed from frozen stocks and plated at a density of 30,000 cells/well in 20 µL growth media (DMEM High Glucose, 10% FBS, 1% Pen Strep/Glu, 100 µg Hygromycin B, 300 µg G418) in clear bottom 384 well plates (e.g., Greiner cat # 981098). After approximately 24 hours incubation in $CO_2$, the cell plate was flicked to discard media, and 10 µL of 20 µM coelenterazine in Assay Buffer was added to cell plates. The cell plates were then loaded into the $CO_2$ incubator on the screening apparatus and after ~2 hours the assay protocol was executed. Compound plates were prepared by adding 35 µL of Assay Buffer (Ham's F12/30 mM Hepes/5 mM $CaCl_2$) to 2 µL of 10 mM compound stocks dissolved in dimethylsulfoxide (DMSO). Agonist was prepared by diluting ATP to 10 µM in assay buffer. The protocol executed on the screening apparatus consists of two additions with concurrent imaging. To the 10 µL of coelenterazine-loaded cells were added 10 µL of diluted compound, followed by 30 µL of agonist. Several seconds before each fluid addition, an image sequence was initiated lasting 30-40 seconds. Following image and signal processing, spatial integration of pixels within each plate well, and temporal integration of the ~10 second peaks, the values of each well were displayed as a pseudocolor matrix.

FIG. 8 shows the output of this luminescence assay. FIG. 8A shows a montage of eight 5-second exposures before, during, and after addition of compounds. FIG. 8B similarly shows response to agonist addition in six 5-second exposures. The values at the top of FIGS. 8A and 8B indicate the brightest and faintest pixel values within the images (in raw CCD units). Bioluminescence intensity kinetics of each of the 384 wells is shown in FIGS. 8D and E. This was computed by integrating signal over the pixels within each well. The temporally integrated responses of each well are displayed in pseudocolor images in FIGS. 8G and H, normalized to percent of control from control wells (defined in the graphical user interface (GUI) of FIG. 13), and using a colorscale shown in FIG. 8I. This data is from the 84th microtiter plate automatically run on the apparatus this day as indicated above A and B, and statistics summarizing quality of the current and all previous plates are plotted in FIGS. 8C and F.

A second example illustrates a fluorescence assay on the same apparatus. Transfected CHO cells, selected for stable expression of an exogenous GPCR, were prepared and seeded as in the previous example, in clear microtiter plates. Instead of coelenterazine, the wells were loaded according to directions provided by Becton, Dickinson & Co, PBX Calcium Dye Kit, Cat. No. 640175. The compound plate was prepared by serially diluting compounds 2:1 from left to right, and the agonist plate had only buffer in the right most two columns.

Figure 14:
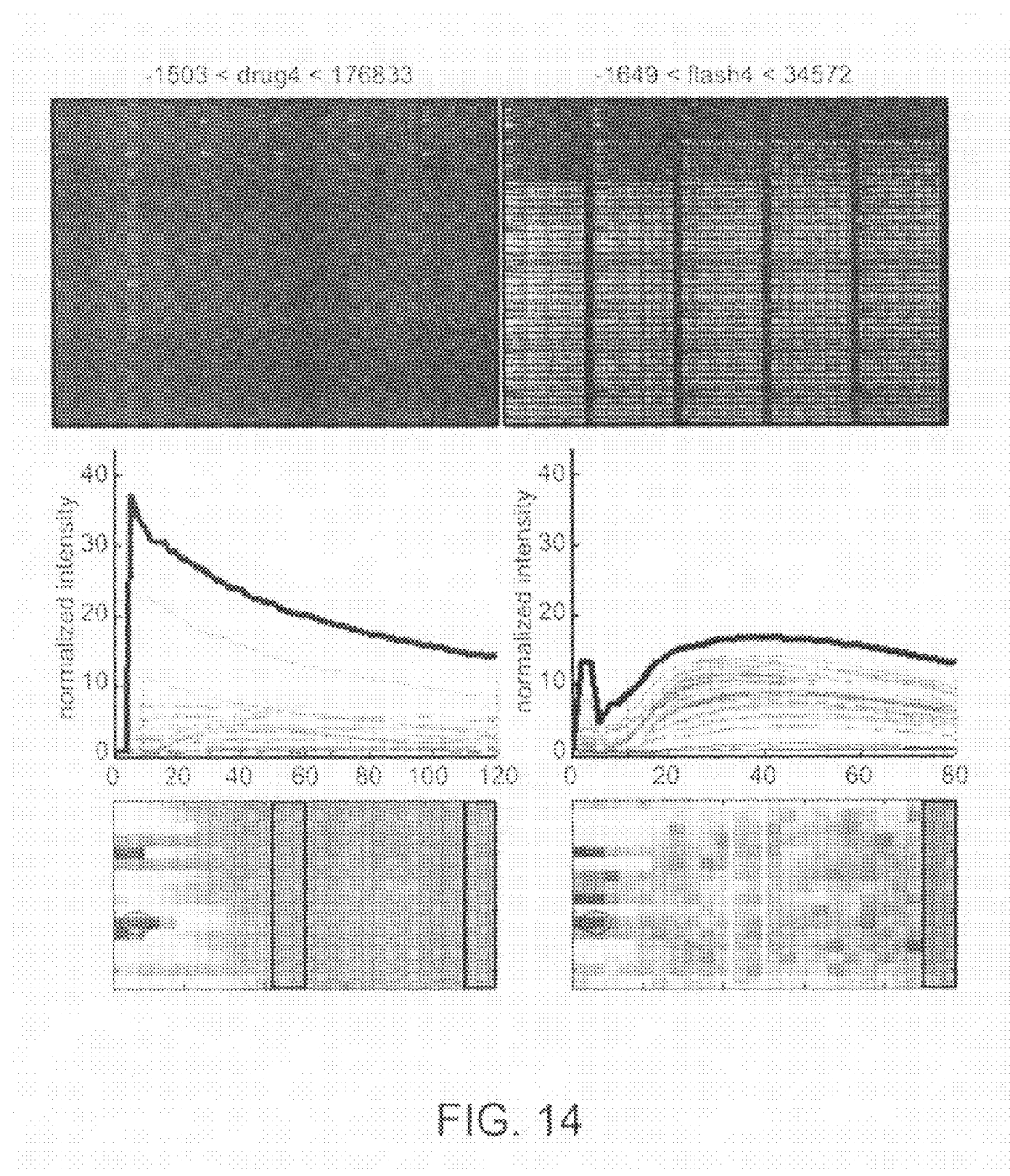
FIG. 14 depicts example output of a fluorescence assay.

Results for the second example fluorescence assay performed on the screening apparatus are provided in FIG. 14. The left column illustrates fluorescence intensity kinetics before, during, and after addition of compounds. The top row shows a montage of image thumbnails and the middle row shows an intensity of the 384 well microtiter plate spatially integrated over each well. The bottom row illustrates spatially and temporally integrated normalized pseudocolor responses of each of the 384 wells, as in the previous figure. The right column shows fluorescence responses to subsequent agonist addition, using the same analysis as the left column. The white rectangle in the graphic at the bottom right (columns 11 and 12 of the 384 well plate) denotes high control wells that received no drug, but agonist in the initial and second fluidic additions respectively. The black rectangle in the graphic at the bottom left (columns 23 and 24 of the 384 well plate) denotes low control wells that received sham compound and agonist (DMSO and buffer respectively). Compound in the top plate row demonstrates weak agonism (left column), but no antagonism (right column). Compound in third row displays weaker agonism and stronger antagonism. Compounds in $4^{th}$ and $6^{th}$ row show no agonism but moderate antagonism. Compound in $11^{th}$ row (circled and bold traces) shows agonism but no antagonism (and inverse antagonism perhaps via allosteric effects). Note the fluorescence images are 3-4 times brighter than the corresponding luminescence images in FIG. 8.

The foregoing description of exemplary embodiments of the invention have been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. An optical array comprising a plurality of optical sandwiches, wherein each optical sandwich comprises:
    (i) a light source;
    (ii) a high numerical aperture collimation lens;
    (iii) an excitation filter selected from the group consisting of a sharp spectral band pass, a low pass filter and a high pass filter; and
    (iv) a diffuser,
wherein the optical elements (i), (ii), (iii) and (iv) are arranged such that an illumination moves from the light source to the collimation lens to the excitation filter to the diffuser, thereby making the illumination spectrally pure and spatially dispersed.

2. The optical array of claim 1, wherein the diffuser of each optical sandwich is a holographic diffuser.

3. The optical array of claim 1, wherein the light source of each optical sandwich is selected from the group consisting of an ultra-bright light emitting diode (LED), a deuterium tube, a flash lamp and an ultraviolet LED, a quartz-tungsten halogen (QTH) bulb, a laser diode, and a fluorescent light source.

4. A plurality of optical arrays of claim 1.

5. The plurality of optical arrays of claim 4, wherein at least two arrays emit light of different wavelength.

6. A rotating shaft comprising a plurality of optical arrays of claim 4.

7. A linear actuator comprising a plurality of optical arrays of claim 4.

8. An apparatus capable of interleaving detection of fluorescence and luminescence emitted from a plurality of samples, the apparatus comprising:
    (a) a sample container receiving device;
    (b) a plurality of optical sandwiches, wherein each optical sandwich comprises:
        (i) a light source;
        (ii) a high numerical aperture collimation lens;
        (iii) an excitation filter selected from the group consisting of a sharp spectral band pass, a low pass filter and a high pass filter; and
        (iv) a diffuser,
    wherein the optical elements (i), (ii), (iii) and (iv) are arranged such that an illumination moves from the light source to the collimation lens to the excitation filter to the diffuser, thereby making the illumination spectrally pure and spatially dispersed; and
    (c) a detector system capable of interleaving detection of fluorescent and luminescent signals emitted from at least one of the plurality of the samples, the detector system comprising: a detector lens; an emission filter; and a single sensor capable of detecting a two dimensional image plane.

9. The apparatus of claim 8, wherein the single sensor is an array detector.

10. The apparatus of claim 8, wherein the single sensor is an imaging detector.

11. An apparatus capable of interleaving detection of fluorescence and luminescence emitted from a plurality of samples, the apparatus comprising:
    (a) a sample container receiving device;
    (b) an optical sandwich comprising:
        (i) a light source;
        (ii) a high numerical aperture collimation lens;
        (iii) an excitation filter selected from the group consisting of a sharp spectral band pass, a low pass filter and a high pass filter; and
        (iv) a diffuser,
    wherein the optical elements (i), (ii), (iii) and (iv) are arranged such that an illumination moves from the light source to the collimation lens to the excitation filter to the diffuser, thereby making the illumination spectrally pure and spatially dispersed; and
    (c) a detector system capable of interleaving detection of fluorescent and luminescent signals emitted from at least one of the plurality of the samples, the detector system comprising: a detector lens; an emission filter; and a single sensor capable of detecting a two dimensional image plane, wherein the detector system is remotely connected to the optical sandwich so that illumination and detection are synchronized.

12. An apparatus capable of interleaving detection of fluorescence and luminescence emitted from a plurality of samples, the apparatus comprising:
    (a) a sample container receiving device;
    (b) a plurality of optical sandwiches arranged in an array, each optical sandwich comprising:
        (i) a light source;
        (ii) a high numerical aperture collimation lens;
        (iii) an excitation filter selected from the group consisting of a sharp spectral band pass, a low pass filter and a high pass filter; and
        (iv) a diffuser,
    wherein the optical elements (i), (ii), (iii) and (iv) are arranged such that an illumination moves from the light source to the collimation lens to the excitation filter to the diffuser, thereby making the illumination spectrally pure and spatially dispersed; and
    (c) a detector system capable of interleaving detection of fluorescent and luminescent signals emitted from at least one of the plurality of the samples, the detector system comprising: a detector lens; an emission filter; and a single sensor capable of detecting a two dimensional image plane.

13. The apparatus of claim 12, further comprising a plurality of optical arrays.

14. The apparatus of claim 13, wherein the plurality of optical arrays are arranged on a linear actuator or on a rotating shaft.

15. The apparatus of any of claims 12, 13 or 14, wherein at least two of the optical sandwiches are positioned on opposing sides of the sample receiving device.

16. The apparatus of claim 13, wherein at least two of the arrays emit a light source of different wavelengths.

17. An apparatus capable of interleaving detection of fluorescence and luminescence emitted from a plurality of samples, the apparatus comprising:
(a) a sample container receiving device;
(b) an optical sandwich comprising:
(i) a light source;
(ii) a high numerical aperture collimation lens;
(iii) an excitation filter selected from the group consisting of a sharp spectral band pass, a low pass filter and a high pass filter; and
(iv) a diffuser,
wherein the optical elements (i), (ii), (iii) and (iv) are arranged such that an illumination moves from the light source to the collimation lens to the excitation filter to the diffuser, thereby making the illumination spectrally pure and spatially dispersed; and
(c) a detector system capable of interleaving detection of fluorescent and luminescent signals emitted from at least one of the plurality of the samples, the detector system comprising: a detector lens; an emission filter; and a single sensor capable of detecting a two dimensional image plane, wherein the emission filter is remotely programmed.

18. An apparatus capable of interleaving detection of fluorescence and luminescence emitted from a plurality of samples, the apparatus comprising:
(a) a sample container receiving device;
(b) an optical sandwich comprising:
(i) a light source;
(ii) a high numerical aperture collimation lens;
(iii) an excitation filter selected from the group consisting of a sharp spectral band pass, a low pass filter and a high pass filter; and
(iv) a diffuser,
wherein the optical elements (i), (ii), (iii) and (iv) are arranged such that an illumination moves from the light source to the collimation lens to the excitation filter to the diffuser, thereby making the illumination spectrally pure and spatially dispersed; and
(c) a detector system capable of interleaving detection of fluorescent and luminescent signals emitted from at least one of the plurality of the samples, the detector system comprising: a detector lens; an emission filter; and a single sensor capable of detecting a two dimensional image plane, wherein the detector lens comprises a remotely controlled lens aperture.

19. An apparatus capable of interleaving detection of fluorescence and luminescence emitted from a plurality of samples, the apparatus comprising:
(a) a sample container receiving device;
(b) a plurality of optical sandwiches arranged in an optical array, each optical sandwich comprising: (i) a light source; (ii) a high numerical aperture collimation lens; (iii) an excitation filter selected from the group consisting of a sharp spectral band pass, a low pass filter and a high pass filter; and (iv) a diffuser, wherein the optical elements (i), (ii), (iii) and (iv) are arranged such that an illumination moves from the light source to the collimation lens to the excitation filter to the diffuser, thereby making the illumination spectrally pure and spatially dispersed; and
(c) a detector system capable of interleaving detection of fluorescent and luminescent signals emitted from at least one of the plurality of samples, the detector system comprising: (i) a detector lens; (ii) an emission filter; and (iii) a sensor.

20. The apparatus of claim 19, wherein the sensor of the detector system is a single sensor capable of detecting a two dimensional image plane.

21. The apparatus of claim 19, further comprising a plurality of optical arrays.

22. The apparatus of claim 21, wherein the plurality of optical arrays are arranged on a linear actuator or on a rotating shaft.

23. The apparatus of any of claims 19, 21, or 22, wherein at least two of the optical sandwiches are positioned on opposing sides of the sample receiving device.

24. The apparatus of claim 21, wherein at least two of the arrays emit a light source of different wavelengths.

25. The apparatus of claim 19, wherein the emission filter is remotely programmed.

26. An apparatus capable of interleaving detection of fluorescence and luminescence emitted from a plurality of samples, the apparatus comprising:
(a) a sample container receiving device;
(b) an optical sandwich comprising: (i) a light source; (ii) a high numerical aperture collimation lens; (iii) an excitation filter selected from the group consisting of a sharp spectral band pass, a low pass filter and a high pass filter; and (iv) a diffuser; and
(c) a detector system capable of interleaving detection of fluorescent and luminescent signals emitted from at least one of the plurality of samples, the detector system comprising: a detector lens; an emission filter; and a single sensor capable of detecting a two dimensional image plane, wherein the emission filter is remotely programmed.

27. The apparatus of claim 26, wherein the optical elements (i), (ii), (iii) and (iv) are arranged such that an illumination moves from the light source to the collimation lens to the excitation filter to the diffuser, thereby making the illumination spectrally pure and spatially dispersed.

* * * * *